United States Patent
Bhat

(10) Patent No.: US 11,397,188 B2
(45) Date of Patent: Jul. 26, 2022

(54) METHOD OF DETECTING AN APP ALZHEIMER'S DISEASE MARKER PEPTIDE IN PATIENTS WITH ALZHEIMER'S DISEASE

(71) Applicant: Krishna Bhat, Galveston, TX (US)

(72) Inventor: Krishna Bhat, Galveston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/940,158

(22) Filed: Mar. 29, 2018

(65) Prior Publication Data

US 2018/0284137 A1    Oct. 4, 2018

Related U.S. Application Data

(60) Provisional application No. 62/478,671, filed on Mar. 30, 2017.

(51) Int. Cl.

| | |
|---|---|
| *A61K 49/00* | (2006.01) |
| *A61K 39/395* | (2006.01) |
| *A61K 49/16* | (2006.01) |
| *G01N 33/53* | (2006.01) |
| *G01N 33/68* | (2006.01) |
| *C07K 16/18* | (2006.01) |
| *C07K 14/47* | (2006.01) |
| *A01K 67/027* | (2006.01) |
| *A01K 67/033* | (2006.01) |
| *A61K 39/00* | (2006.01) |

(52) U.S. Cl.
CPC ...... *G01N 33/6896* (2013.01); *C07K 14/4711* (2013.01); *C07K 16/18* (2013.01); *A01K 67/0275* (2013.01); *A01K 67/0339* (2013.01); *A01K 2217/05* (2013.01); *A01K 2227/105* (2013.01); *A01K 2227/706* (2013.01); *A01K 2267/0312* (2013.01); *A61K 39/3955* (2013.01); *A61K 49/0008* (2013.01); *A61K 2039/505* (2013.01); *C07K 2317/34* (2013.01); *G01N 2333/4709* (2013.01); *G01N 2800/2814* (2013.01); *G01N 2800/2821* (2013.01)

(58) Field of Classification Search
CPC ....... G01N 2800/2821; G01N 33/6896; G01N 2333/4709; G01N 2500/00; G01N 2800/52; G01N 2800/2814; G01N 33/5023; G01N 33/551; G01N 33/68; C07K 16/18; C07K 14/4711; A61K 39/3955; A61K 39/505; A61K 39/00; A61K 47/6425; A61K 49/0008; C12Q 1/37; C12P 21/00; Y02A 50/41; Y02A 50/464; Y02A 50/472; Y02A 50/489
See application file for complete search history.

(56) References Cited

U.S. PATENT DOCUMENTS

| | | | | |
|---|---|---|---|---|
| 7,723,117 | B2 * | 5/2010 | Delacourte | ........ G01N 33/6896 436/86 |
| 7,772,375 | B2 * | 8/2010 | Greferath | ................ A61P 21/02 530/388.85 |
| 7,932,048 | B2 * | 4/2011 | Mendez | .................. C07K 16/18 435/7.9 |
| 9,255,932 | B2 * | 2/2016 | Sarasa Barrio | ........ C07K 16/18 |
| 9,863,961 | B2 * | 1/2018 | Sarasa Barrio | .... G01N 33/6896 |
| 2007/0066527 | A1 * | 3/2007 | Tezapsidis | ............. A61K 38/17 514/5.8 |
| 2012/0244156 | A1 * | 9/2012 | Tezapsidis | ............. A61K 38/17 424/134.1 |
| 2013/0183309 | A1 * | 7/2013 | Tezapsidis | ............. A61K 38/17 424/134.1 |
| 2014/0024054 | A1 * | 1/2014 | Sarasa Barrio | ........ C07K 16/18 435/7.92 |
| 2016/0195548 | A1 * | 7/2016 | Sarasa Barrio | ........ C07K 16/18 435/7.21 |
| 2018/0057552 | A1 * | 3/2018 | Willem | .............. G01N 33/6896 |

FOREIGN PATENT DOCUMENTS

| | | | | |
|---|---|---|---|---|
| EP | 391714 | * | 10/1990 | ............. G01N 33/68 |
| EP | 2511296 | * | 4/2011 | |
| WO | WO200237118 | * | 5/2002 | |
| WO | WO2006095041 | * | 9/2006 | |
| WO | WO2007068412 | * | 6/2007 | |

OTHER PUBLICATIONS

Zhang et al. Mol. Brain 2011; 4:3.*
Wolf et al. The EMBO J., 1990; 9:2079-2084.*
Vassar et al., Science, 1999; 286:735-741.*
Nunan et al. Eur. J. Biochem. 2001; 268:5329-5336.*
Muphy et al. J. Alzheimers Dis. 2010; 19:311. doi:10.3233/JAD-2010-1221.*
van der Kant et al. Developmental Cell; 2015; 32:502-515.*
Garcia-Ayllon et al. Scitific Reports, 2017; 7:2477. DOI:10.1038/s41598-017-02841-7.*
Bayer et al. Front. Aging Neurosci. 2010; doi:10.3389/fnagi.2010.00008.*
Eggert et al. J. Biol. Chem. 2004; 279:18146-18156.*
Chang et al. J. Biol. Chem. 2003; 278:51100-51107.*
Matsumoto et al. Eur. J. Biochem. 1994; 225:1055-1062.*
Matsumoto et al. Eur. J. Biochem. 19934; 217:21-27.*
Selkoe et al., Proc. Natl. Acad. Sci. USA 1988; 85:7341-7345.*
Kaneko et al. Proc. Jpn. Acad., Ser. B, 2014; 90:104-117.*

(Continued)

*Primary Examiner* — Chang-Yu Wang

(57) ABSTRACT

Certain embodiments are directed to marker peptides or marker peptide antibodies can be used in producing diagnostic kits or used in diagnostic methods for Alzheimer's disease. The antibodies and/or marker peptides can be used in immunohistochemical and biochemical methods for qualitative and quantitative analysis of marker peptide levels and/or localization in brain samples and CSF samples.

8 Claims, 14 Drawing Sheets

Specification includes a Sequence Listing.

(56) References Cited

OTHER PUBLICATIONS

The Western blot method published on the human protein Atlas website on Mar. 8, 2015, retrieved from the wayback machine website: https://web.archive.org/web/20150308102435/https://www.proteinatlas.org/learn/method/western+blot on Mar. 25, 2019.*
Shanthi et al. SAGE Open Medicine 2015; 3:2050312115598250. DOI:10.1177/2050312115598250.*
Das, Master's thesis, Biotechnology—Master's program, Department of Molecular Biology, Uppsala 2012, Swedish University of Agricultural Science.*
Guo et al., PNAS 2004; 101:9205-9210.*
Alaoui-Ismaili et al., Cytokine Growth Factor Rev. 2009; 20:501-507.*
Pawson et al. 2003, Science 300:445-452.*
Burgess et al. J of Cell Bio. 1990, 111:2129-2138.*
Rudikoff et al. Proc. Natl. Acad. Sci. USA 1982 vol. 79: p. 1979.*
Grant et al. PloS One, 14(2): 40212815. doi.org/10.1371/journal.pone.0212815, Feb. 28, 2019.*
Antigenicity of SEQ ID No. 18 from http://tools.immuneepitope.org/bcell/result/.*
The factsheet of an anti-Abeta1-17 polyclonal antibody from the Genscript company website: www.genscript.com/antibody/A00685-_Amyloid_Antibody_1_17_pAb_Rabbit.html retrieved on Jan. 3, 2019.*
Ancolio et al., PNAS, 1999;96:4119-4124.*
Barelli et al. Mol. Med. 1997; 3:695-707.*
Aisen and Davis, "Inflammatory Mechanisms in Alzheimer's Disease: Implications for Therapy" Am J. Psychiatry, 1994; 151:(8): 1105-1113.
Alekseyenko et al. "Targeted manipulation of serotonergic neurotransmission affects the escalation of aggression in adult male Drosophila melanogaster," PloS One, 2010; 5(5): e10806, 11 pages.
Benilova et al. "The toxic Aβ oligomer and Alzheimer's disease: and emperor in need of clothes" Nature Neuroscience, 2012; 15(3): 349-357.
Biscaro et al. "Inhibition of Microglial Activation Protects Hippocampal Neurogenesis and Improves Cognitive Deficits in a Transgenic Mouse Model for Alzheimer's Disease," Neurodegenerative Dis. 2012; 9: 187-198.
Bonner and Boulianne, "Drosophila as a model to study age-related neurodegenerative disorders: Alzheimer's disease," Experimental Gerontology, 2011; 46: 335-339.
Botas, Juan. "Drosophila researchers focus on human disease," Nature Genetics, 2007; 39(5): 589-591.
Carmine-Simmen et al. "Neurotoxic effects induced by the Drosophila amyloid-β peptide suggest a conserved toxic function," Neurobiology of Disease, 2009; 33:274-281.
Chakraborty et al. "Characterization of a Drosophila Alzheimer's Disease Model: Pharmacological Rescue of Cognitive Defects," PLoS One, 2011; 6(6): e20799, 13 pages.
Chartier-Harlin et al. "Early-onset Alzheimer's disease caused by mutations at codon 717 of the β-amyloid precursor protein gene," Nature, 1991; 353: 844-846.
Cohen et al. "A Transgenic Alzheimer Rat with Plaques, Tau Pathology, Behavioral Impairment, Oligomeric Aβ, and Frank Neuronal Loss," The Journal of Neuroscience, 2013; 33(15): 6245-6256.
Gama Sosa et al. "Modeling human neurodegenerative diseases in transgenic systems," Hum. Genet. 2012; 131: 535-563.
Gandy et al. "Alzheimer Aβ Vaccination of Rhesus Monkeys (Macaca mulatta)" Alzhimer Dis Assoc Disord, 2004; 18: 44-46.
Gazi et al. "A neurodegenerative disease affecting synaptic connections in Drosophila mutant for the tumor suppressor morphogen Patched," Developmental Biology, 2009; 334: 311-323.
Giusti-Rodriguez et al. "Synaptic deficits are rescued in the p25/Cdk5 model of neurodegeration by the reduction of the β-secretase (BACE1)" J. of Neuroscience, 2011; 31(44): 15751-15756.

Goate et al. "Segregation of a missense mutation in the amyloid precursor protein gene with familial Alzheimer's disease" Nature, 1991; 349: 704-706.
Greeve et al., "Age-Dependent Neurodegeneration and Alzheimer-Amyloid Plaque Formation in Transgenic Drosophila," The Journal of Neuroscience, 2004; 24(16): 3899-3906.
Halder et al. "Induction of ectopic eyes by targeted expression of the eyeless gene in Drosophila," Science, 1995; 267: 1788-1792.
Hall and Roberson. "Mouse models of Alzheimer's disease," Brain Research Bulletin, 2012; 88:3-12.
Hardy and Selkoe, "The Amyloid Hypothesis of Alzheimer's Disease: Progress and Problems on the Road to Therapeutics," Science, 2002; 297(5580): 353-356.
Harvey et al. "The prevalence and causes of dementia in people under the age of 65 years," J. Neurol. Neurosurg. Psychiatry, 2003; 74: 1206-1209.
Hua et al. "Toxicity of Alzheimer's disease-associated Aβ peptide is ameliorated in a Drosophila model by tight control of zinc and copper availability," Biol. Chem., 2011; 392: 919-926.
Hung et al. "Amyloid-β peptide (Aβ) Neurotoxicity Is Modulated By The rate of Peptide Aggregation: Aβ Dimers and Trimers Correlate with Neurotoxicity," J. of Neuroscience, 2008; 28(46): 11950-11958.
Jahn et al. "Detection of early locomotor abnormalities in a Drosophila model of Alzheimer's disease," Journal of Neuroscience Methods, 2011; 197: 186-189.
Johard et al. "Peptidergic clock neurons in Drosophila: ion transport peptide and short neuropeptide F in subsets of dorsal and ventral lateral neurons," The Journal of Comparative Neurobiology, 2009; 516: 59-73.
Jonsson et al. "A mutation in APP protects against Alzheimer's disease and age-related cognitive decline" Nature, 2012; 488; 96-99.
Kim et al. "Potential late-onset Alzheimer's disease-associated mutations in ths ADAM10 gene attenuate α-secretase activity," Human Molecular Genetics, 2009; 18(20): 3987-3996.
Leon et al. "A Novel Transgenic Rat Model with a Full Alzheimer's-Like Amyloid Pathology Displays Pre-Plaque Intracellular Amyloid-β-Associated Cognitive Impairment," Journal of Alzheimer's Disease, 2010; 20: 113-126.
Lijima et al. "Dissecting the pathological effects of a human Aβ40 and Aβ42 in Drosophila: A potential model for Alzheimer's disease," PNAS, 2004; 101(17): 6623-6628.
Lijima-Ando et al. "Mitochondrial mislocalization underlies Aβ42-induced neuronal dysfunction in a Drosophila model of Alzheimer's disease" Plos One, 2009; 4(12): e8310, 13 pages.
Liu and Davis, "The GABAergic anterior paired lateral neuron suppresses and is suppressed by olfactory learning," Nature Neuroscience, 2009; 12(1): 53-59.
Liu et al. "A transgenic rat that develops Alzheimer's disease-like amyloid pathology, deficits in synaptic plasticity and cognitive impairment," Neurobiology of Disease, 2008; 31: 46-57.
Lobsiger and Cleveland. "Glial cells as intrinsic components of non-cell-autonomous neurodegenerative disease," Nature Neuroscience, 2007; 10:11, 1355-1360.
Lobsiger et al. "Schwann cells expressing dismutase active mutant SOD1 unexpectedly slow disease progression in ALS mice," PNAS, 2009; 106(11): 4465-4470.
Luo et al. "Human Amyloid Precursor Protein Ameliorates Behavioral Deficit of Flies Deleted for Appl Gene," Neuron, 1992; 9: 595-605.
Manavalan et al. "The Midline Protein Regulates Axon Guidance by Blocking the Reiteration of Neuroblast Rows withing the Drosophila Ventral Verve Cord," PLoS One, 2013; 9(12): e1004050, 15 pages.
McGowan et al. "Aβ42 is Essential for Parenchymal and Vascular Amyloid Deposition in Mice," Neuron, 2005; 47: 191-199.
McLendon et al. "Cell-free assays for γ-secretase activity," The FASEB Journal, 2000; 14(15): 21 pages.
Nelson et al. "Alzheimer's disease is not "brain aging": neuropathological, genetic, and epidemiological human studies," Acta Neruopathol, 2011; 121: 571-587.

(56) References Cited

OTHER PUBLICATIONS

Nelson et al. "Correlation of Alzheimer Disease Neuropathologic Changes with Cognitive Status: A Review of the Literature," *J. Neuropathol. Exp. Neurol.* 2012; 71(5): 362-381.
Nussleing-Volhard and Weichaus, "Mutations affecting segment number and polarity in *Drosophila*" *Nature*, 1980; 287: 795-801.
Nusslein-Volhard et al. "Mutations affecting the pattern of the larval cuticle in *Drosophila melanogaster,*" *Roux's Arch. Dev. Biol.* 1984; 193: 267-282.
Palop and Mucke, "Amyloid-β-induced neuronal dysfunction in Alzheimer's disease: from synapses toward neural networks," *Nature Neuroscience*, 2010; 13(7): 812-818.
Parent et al. "Presenilin attenuates receptor-mediated signaling and synaptic function," *Journal of Neuroscience*, 2005; 25(6): 1540-1549.
Price and Sisodia, "Mutant Genes in Familial Alzheimer's Disease and Transgenic Models," *Annu. Rev. Neurosci.* 1998; 21: 479-505.
Prüßing et al. "*Drosophila* melanogaster as a model organism for Alzheimer's disease" *Molecular Neurodegeneration*, 2013; 8(35): 11p.
Rajan and Perrimon, "*Drosophila* Cytokine Unpaired 2 Regulates Physiological Homeostasis by Remotely Controlling Insulin Secretion," *Cell*, 2012; 151: 123-137.
Ren et al. "A GABAergic Inhibitory Neural Circuit Regulates Visual Reversal Learning in *Drosophila,*" *The Journal of Neuroscience*, 2012; 32(34): 11524-11538.
Rincon-Limas et al. "*Drosophila* Models of Proteinopathies: the Little Fly that Could," *Current Pharmaceutical Design*, 2012; 18: 1108-1122.
Shapiro and Scherer, "the crystal structure of a complement-1q family protein suggests an evolutionary link to tumor necrosis factor" *Current Biology*, 1998; 8(6): 335-338.
Soldano et al. "The *Drosophila* homologue of the amyloid precursor protein is a conserved modulator of Wnt PCP signaling," *PLoS One*, 2013; 11(5): e1001562. 13 pages.
Sosa et al. "Dosage of amyloid precursor protein affects axonal contact guidance in Down syndrome" *the FASEB Journal*, 2014; 28: 195-205.
Speretta et al. "Expression in *Drosophila* of Tandem Amyloid β Peptides Provides Insights into Links between Aggregation and Neurotoxicity," *The Journal of Biological Chemistry*, 2012; 287(24): 20748-20754.
Suh et al. "ADAM10 Missense Mutations Potentiate β-Amyloid Accumulation by Impairing Prodomain Chaperone Function," *Neuron*, 2013; 80: 385-401.
Suzuki et al. "An Increased Percentage of Long Amyloid β Protein Secreted by Familial Amyloid β Protein Precursor (βAPP$_{717}$) Mutants," *Science*, 1994; 264: 1336-1340.
Tan et al. "The Toll—NFκB Signaling Pathway Mediates the Neuropathological Effects of the Human Alzheimer's Aβ42 Polypeptide in *Drosophila*" *PLoS One*, 2008; 3(12): e3966, 10 pages.
Tanaka et al., "Neuronal Assemblies of the *Drosophila* Mushroom Body," *The Journal of Comparative Neurology*, 2008; 508: 711-755.
Townsend, Matthew. "When Will Alzheimer's Disease be Cured? A Pharmaceutical Perspective," *Journal of Alzheimer's Disease*, 2011; 24: 43-52.
Van Dam et al. "Animal models in the drug discovery pipeline for Alzheimer's disease," *British Journal of Pharmacology*, 2011; 164: 1285-1300.
von Bernhardi, Rommy. "Glial Cell Dysregulation: a New Perspective on Alzheimer Disease," *Neurotoxicity Research*, 2007; 12(4): 215-232.
Walker et al. "Molecular mechanisms of cognitive dysfunction following traumatic brain injury," *Frontiers in Aging Neuroscience*, 2013; 5(29): 1-25.
Yagi et al. "Overexpression of Human Amyloid Precursor Protein in *Drosophila,*" *Molecular Cell Biology Research Communications*, 2000; 4(1): 43-49.
Yamanaka et al. "Astrocytes as determinants of disease progression in inherited amyotrophic lateral sclerosis," *Nature Neuroscience*, 2008; 11(3): 251-253.
Yan et al. "Membrane-anchored aspartyl protease with Alzheimer's disease β-secretase activity," *Nature*, 1999; 402: 533-537.

\* cited by examiner

FIGS. 1A-I

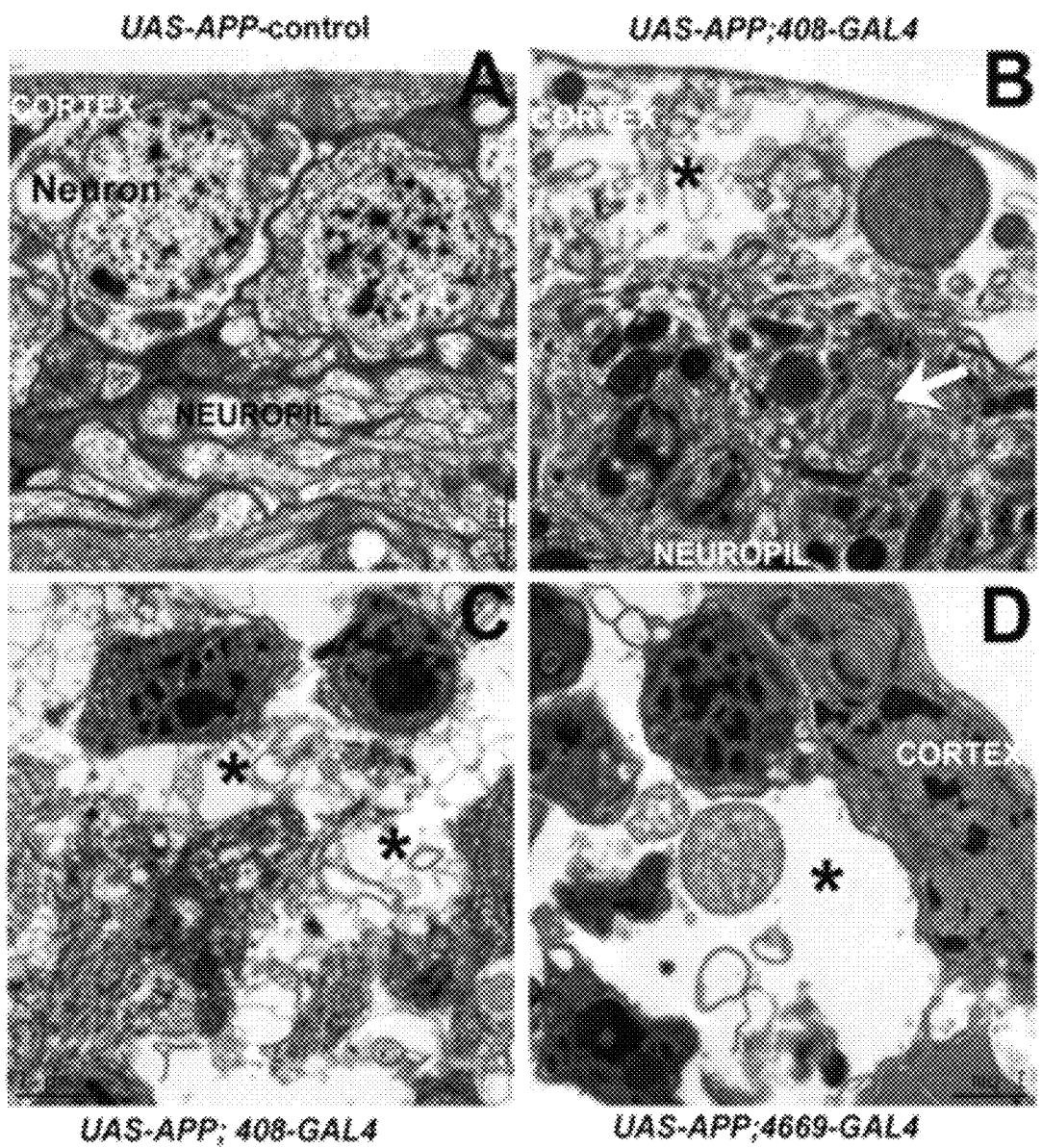
FIGS. 3A-D

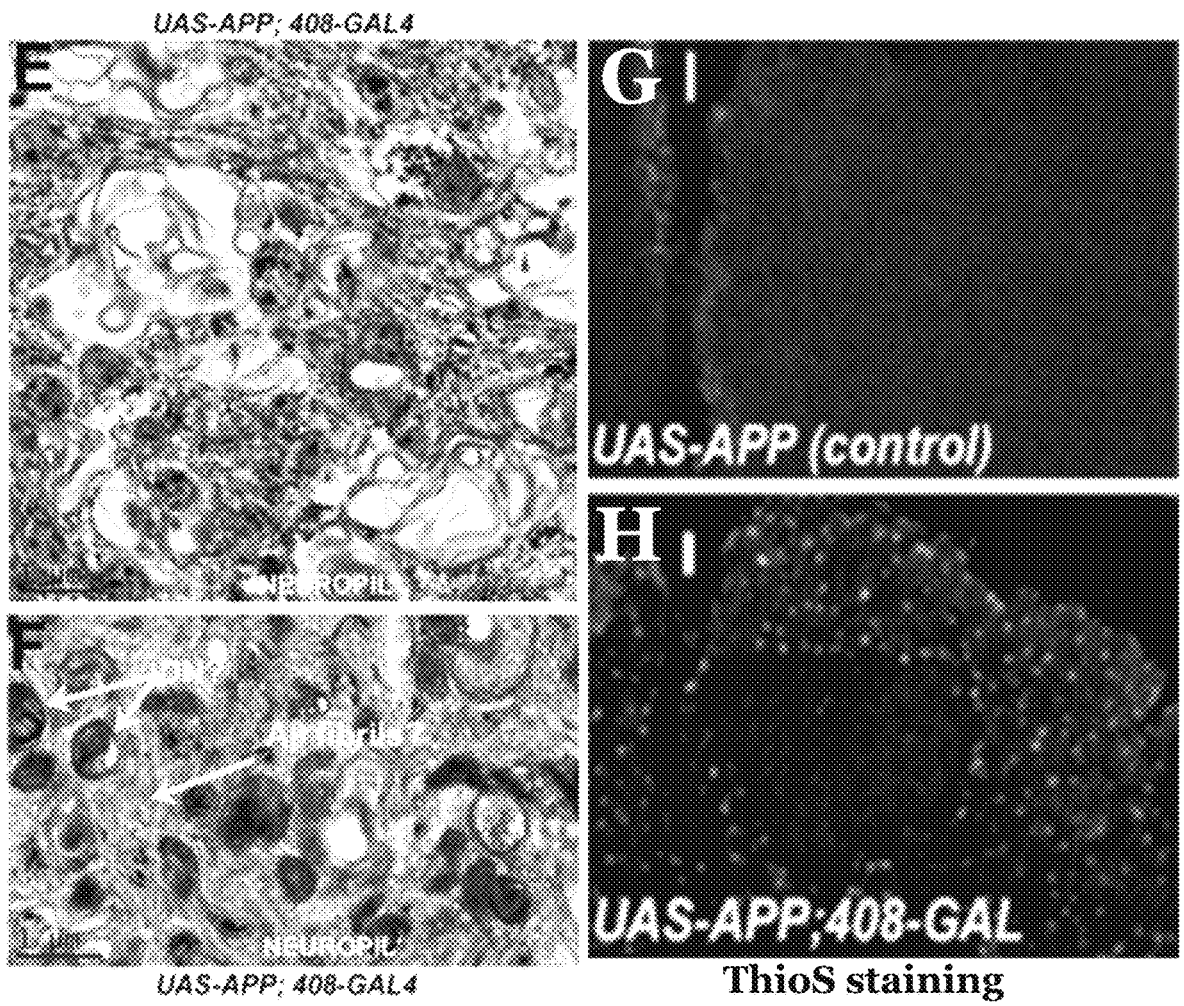
FIGS. 3E-H

Protease cutting sites in _D A E F R H D S G Y E V H H Q K L (SEQ ID NO:18):_

| Name of enzyme | No. of cleavages | Positions of cleavage sites |
| --- | --- | --- |
| Arg-C proteinase | 1 | 5 |
| Asp-N endopeptidase | 1 | 6 |
| Asp-N endopeptidase + N-terminal Glu | 3 | 2 6 10 |
| Caspase 1 | 1 | 7 |
| Chymotrypsin-high specificity (C-term to [FYW], not before P) | 2 | 4 10 |
| Chymotrypsin-low specificity (C-term to [FYWML], not before P) | 5 | 4 10 13 14 17 |
| Clostripain | 1 | 5 |
| Formic acid | 2 | 1 7 |
| Glutamyl endopeptidase | 2 | 3 11 |
| LysC | 1 | 16 |
| LysN | 1 | 15 |
| Pepsin (pH1.3) | 3 | 3 4 17 |
| Pepsin (pH>2) | 5 | 3 4 9 10 17 |
| Proteinase K | 7 | 2 3 4 10 11 12 17 |
| Staphylococcal peptidase I | 2 | 3 11 |
| Thermolysin | 1 | 16 |
| Trypsin | 2 | 5 16 |

FIG. 7

APP-12-100 aa peptide –Trypsin site (at K)

*GCAAAGAGGA GCAGCGGCCG CAAAAC ATG C TG CCC GGT TT G GCA CTG CTC CTG CTG GCC G CC TGG ACG GC T CGG GCG* ACG GAG GAG ATC TCT GAA GTG AAG ATG GAT GCA GAA TTC CGA CAT GA CTCAGGATAT GAAGTTCATC ATCAAAAATT GGTGTTCTTT GCAGAAGATG TGGGTTCAAA CAAAGGTGCA ATCATTGGAC TCATGGTGGG CGGTGTTGTC ATAGCGACAG TGATCGTCAT CACCTTGGTG ATGCTGAAGA AGAAACAGTA CACATCCATT CATCATGGTG TGGTGGAGGT TGACGCCGCT GTCACCCAG AGGAGCGCCA CCTGTCCAAG ATGCAGCAGA ACGGCTACGA AAATCCAACC TACAAGTTCT TTGAGCAGAT GCAGAAC TAG ACCCCCTAGG CCACAGCTCG AGCAGCCTCT GAA SEQ ID NO:7)

K E E Q R P Q N *Met L P G L A L L L L A A W T A R A* T E E I S E V K Met *D A E F R H D S G Y E V H H Q K L V F F A E D V G S N K G A I I G L Met V G G V V I A T V I V I T L V Met L K K K Q Y T S I H H G V V E V D A A V T P E E R H L S K Met Q Q N G Y E N P T Y K F F E Q Met Q N* Stop T P Stop (SEQ ID NO:8)

APP-12-100 transgenic line data

Western

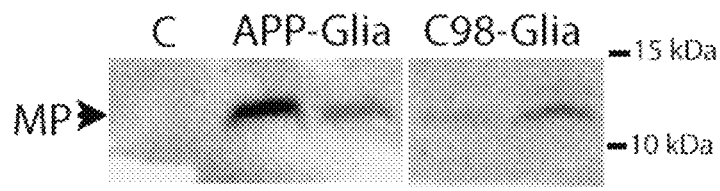

FIG. 9

APP-12-94 aa peptide

GCAAAGAGGA GCAGCGGCCG CAAAAC *ATG C TG CCC GGT TT G GCA CTG CTC CTG CTG GCC G CC TGG ACG GC T CGG* CAT GA CTCAGGATAT GAAGTTCATC ATCAAAAATT GGTGTTCTTT GCAGAAGATG TGGGTTCAAA CAAAGGTGCA ATCATTGGAC TCATGGTGGG CGGTGTTGTC ATAGCGACAG TGATCGTCAT CACCTTGGTG ATGCTGAAGA AGAAACAGTA CACATCCATT CATCATGGTG TGGTGGAGGT TGACGCCGCT GTCACCCCAG AGGAGCGCCA CCTGTCCAAG ATGCAGCAGA ACGGCTACGA AAATCCAACC TACAAGTTCT TTGAGCAGAT GCAGAAC TAG ACCCCTAGG CCACAGCTCG AGCAGCCTCT GAA (SEQ ID NO:9)

K E E Q R P Q N *M L P G L A L L L L A A W T A R* --H D S G Y E V H H Q K L V F F A E D V G S N K G A I I G L Met V G G V V I A T V I V I T L V Met L K K K Q Y T S I H H G V V E V D A A V T P E E R H L S K Met Q Q N G Y E N P T Y K F F E Q Met Q N Stop T P Stop (SEQ ID NO:10)

(Between R and H is a Trypsin site as well as an Arg-C proteinase site; between H and D is Asp-endopeptidase site)

FIG. 10

METHOD OF DETECTING AN APP ALZHEIMER'S DISEASE MARKER PEPTIDE IN PATIENTS WITH ALZHEIMER'S DISEASE

PRIORITY PARAGRAPH

The present application claims priority to U.S. Application No. 62/478,671 filed Mar. 30, 2017, which is incorporated herein by referenced in its entirety.

STATEMENT OF GOVERNMENT SUPPORT

This invention was made with United States Government support under NS09136701, awarded by the National Institutes of Health and the National Institute of Neurological Disorders and Stroke. The United States Government has certain rights in the invention.

BACKGROUND

Alzheimer's disease (AD) is the leading cause of dementia in the elderly (Mayo Clinic, Alzheimer's, 2014). AD afflicts an estimated 5 million Americans and is rapidly increasing in prevalence as the population ages. Although its symptoms can be treated, AD remains an incurable and fatal disorder. AD is a complex disease that can involve amyloid aggregation, increased amyloid secretion, increased amyloid production, neuritic plaques, loss of normal physiological functions of amyloid, hyperphosphorylation of tau, increased neurofibrillary tangles, increased toxic species of tau, increased levels of tau, and neuro-inflammation. The disease manifests itself through decreased cognition, memory impairment, confusion, visual impairment, impairment of spatial recognition, reduced vocabulary, depression, and changes in mood (Mayo Clinic, Alzheimer's, 2014).

There are no specific markers for detecting Alzheimer's disease. While the Amyloid Precursor Protein (APP) is involved in the disease, it is widely thought that the processed Aβ42 peptide is responsible for the disease/neurodegeneration. Current treatments for AD include those that assist in boosting levels of cell-to-cell communication, such as cholinesterase inhibitors, acetylcholinesterase inhibitors, and memantine. (Mayo Clinic, Alzheimer's, 2014).

There remains a need for additional biomarkers and therapies for AD, as well as better understanding of the disease process.

SUMMARY

Certain embodiments of the invention are directed to one or more marker peptides that are associated with lethality and neuropathology of Alzheimer's disease (AD), and methods and kits using or comprising the same. In certain aspects a marker peptide is specific for Alzheimer's disease (AD). In certain embodiments the marker peptide is complexed with an antibody for detection purposes or coupled to a substrate or isolated in a gel. In a further aspect the marker peptide is a processed peptide of Amyloid Precursor Protein (APP). The marker peptide is not APP C99 (SEQ ID NO:13) or APP C83. In certain aspects an APP C99 and APP C83 peptide are specifically excluded. Accordingly, disclosed herein are compositions and methods related to the marker peptides for diagnosing, treating, and preventing AD.

Certain embodiments are directed to methods of detecting an APP Alzheimer's disease marker peptide. In certain aspects the methods can comprise (a) obtaining a biological sample from a human subject; (b) size fractionating proteins from the sample; and (c) detecting whether the APP Alzheimer's disease marker peptide is present in the sample by contacting the size fractionated proteins with an antibody that binds a peptide comprising an amino acid sequence of SEQ ID NO:2, SEQ ID NO:4, SEQ ID NO:6, SEQ ID NO:8, SEQ ID NO:10, or SEQ ID NO:18, and detecting binding of the antibody to the APP Alzheimer's disease marker peptide between the 10 kDa and 15 kDa protein fractions. In a particular embodiment the APP fragment detected consists of the amino sequence of SEQ ID NO:8 or SEQ ID NO:10. Protein fractionation can be done by size exclusion chromatography, gel electrophoresis, or other size fraction techniques known in the art. In certain aspects protein fractionation is by denaturing polyacrylamide gel electrophoresis. The methods can further comprise transferring the size fractionated proteins to a detection support, such as a Western blot membrane. The APP Alzheimer's disease marker peptide can have an approximate molecular weight of 12 kDa±4 kDa. In certain embodiments the sample need not be size fractionated if a 12 kDa marker protein specific antibody is used. In certain aspects the biological sample is plasma, cerebrospinal fluid (CSF), brain tissue, neuronal tissue, or muscle tissue. In certain aspects immunoprecipitation prior to processing (e.g., size fractionation) with an antibody can be performed for detection purposes. In a further aspect more than one specific antibody can be used for immunoprecipitation and/or detection to increase specificity. The antibody or antibodies can comprise a detectable agent or label. In certain aspects the detectable agent is a radioactive marker, a nucleic acid, a fluorescent label, or an enzymatic label.

In a particular embodiment the antibody specifically binds a peptide having an amino acid sequence of SEQ ID NO:18 or 4, 5, 6, 7, 8, 9, 10, 11, 12, 13, 14, 15, or 16 consecutive amino acids or SEQ ID NO:18 beginning from amino acid 1, 2, 3, 4, 5, 6, 7, 8, 9, 10, 11, or 12 of SEQ ID NO:18, in certain embodiments the epitope can be a conformation epitope that recognizes a free amino terminal end of an APP (SEQ ID NO:18) fragment.

Other embodiments are directed to methods of evaluating a patient suspected of or having Alzheimer's disease comprising the step of detecting binding of a marker peptide antibody to a marker peptide in a biological sample from the subject or patient, wherein the detection of the marker peptide or a marker peptide binding antibody in the biological sample is indicative of Alzheimer's disease. In certain aspects detecting a marker peptide is by immunoassay or immunohistochemistry, or immunoassay or immunohistochemistry following immunoprecipitation. The biological sample can be plasma, cerebrospinal fluid (CSF), brain tissue, neuronal tissue, or muscle tissue. In certain aspects the marker peptide or the marker peptide antibody comprises a detectable agent or label. The detectable agent can be a radioactive marker, a nucleic acid, a fluorescent label, or an enzymatic label. In certain embodiment the marker peptide comprises, consists essentially of, or consists of an amino acid sequence SEQ ID NO:2, SEQ ID NO:4, SEQ ID NO:6, SEQ ID NO:8, SEQ ID NO:10, or SEQ ID NO:18. In particular aspects the APP Alzheimer's disease marker peptide has an amino acid sequence that is 90, 95, 98, 99, or 100% identical to 110, 111, 112, 113, 114, 115, 116, 117, 118, 119, 120, 121, 122, 123, 124, 125, 126, 127, 128, 129, 130, 131, 132, 133 consecutive amino acids of SEQ ID NO:8 or SEQ ID NO:10.

Certain aspects are directed to a diagnostic kit for Alzheimer's disease comprising (a) an isolated APP Alzheimer's disease marker peptide between the 10 kDa and 15 kDa having an amino acid sequence consisting of 20 to 130 contiguous amino acids of SEQ ID NO:2, and (b) an antibody that binds APP Alzheimer's disease marker peptide between the 10 kDa and 15 kDa. The marker peptide can have an amino acid sequence SEQ ID NO:2, SEQ ID NO:4, SEQ ID NO:6, SEQ ID NO:8, or SEQ ID NO:10. In certain aspects the marker peptide is coupled to a support. In a further aspect the support is a bead, membrane, microtiterplate, or glass slide. The antibody can be coupled to a detectable agent or label. In certain aspects the detectable agent is a radioactive marker, a nucleic acid, a fluorescent label, or an enzymatic label.

Embodiments of the invention can also include transgenic animals expressing an approximately 12 kDa APP Alzheimer's disease marker peptide consisting of an amino acid sequence of SEQ ID NO:2, SEQ ID NO:4, SEQ ID NO:6, SEQ ID NO:8, or SEQ ID NO:10. The transgenic animal can be a mammal or an insect. In certain aspects the transgenic animal is a fruit fly or a mouse.

Other aspects of the invention are directed to methods of making a conformation specific antibody comprising administering an immunogenic composition comprising approximately 12 kDa APP Alzheimer's disease marker peptide consisting of an amino acid sequence of SEQ ID NO:2, SEQ ID NO:4, SEQ ID NO:6, SEQ ID NO:8, or SEQ ID NO:10 to a mammal and selecting for an antibody that specifically binds the marker peptide.

Certain embodiments are directed to a conformation specific antibody that specifically binds an approximately 12 kDa APP Alzheimer's disease marker peptide consisting of an amino acid sequence of SEQ ID NO:2, SEQ ID NO:4, SEQ ID NO:6, SEQ ID NO:8, or SEQ ID NO:10. A further embodiment is directed to methods for screening for or identifying a therapeutic agent for Alzheimer's disease, the method comprising the steps of contacting cells expressing the marker peptide with an agent to be screened; and determining a change in the amount or stability of the peptide or the toxicity of the peptide to the cell when the cell is contacted with a putative therapeutic agent. In certain aspects the cell is in a transgenic animal.

Still other embodiments are directed to an antibody that binds or specifically binds a marker peptide.

Certain embodiments are directed to a diagnostic reagent for Alzheimer's disease, the reagent comprising a marker peptide or an antibody that binds a marker peptide.

Certain embodiments are directed to a diagnostic marker peptide for Alzheimer's disease, the peptide having an amino acid sequence comprising, consisting of, or consisting essentially of 5, 10, 20, 25, 30, 35, 40, 50, 55, 60, or 65 to 70, 75, 80, 85, 90, 95, 100, 105, 110, 115, 120, 125, or 130 contiguous amino acids of SEQ ID NO:2, 4, 6, 8, or 10 including all appropriate values and ranges there between. In particular embodiments the peptide is about 12 kDa±4 kDa. In certain aspects the marker peptide has an amino acid sequence comprising, consisting essentially of, or consisting of the amino acid sequence of SEQ ID NO:2, SEQ ID NO:4, SEQ ID NO:6, SEQ ID NO:8, or SEQ ID NO:10. The marker peptide can be coupled to a support and/or a detectable agent or label. In certain aspects the support is a biochip, membrane, microtiterplate, or glass slide.

The term "effective concentration" or "effective amount" is defined as a sufficient amount to cause a measurable change in at least one parameter, such as a decrease in at least one symptom of Alzheimer's disease.

The terms "inhibiting," "reducing," or "prevention," or any variation of these terms, when used in the claims and/or the specification includes any measurable decrease or complete inhibition of the parameter, such as a symptom of Alzheimer's disease.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, devices, compositions, and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE FIGURES

The following drawings form part of the present specification and are included to further demonstrate certain aspects of the present invention. The invention may be better understood by reference to one or more of these drawings in combination with the detailed description of the specification embodiments presented herein.

FIGS. 3A-H. Neuropathology in the adult brain expressing hAPP. Electron micrographs of the central brain cortical and neuropil regions from the control and APP-GOF brains. In Panel F, Aβ fibrils and dystrophic neurites (DN) are shown, as judged by comparing to similar structures found in senile plaques in AD and in Aβ seeded APP/PS1-transgenic mouse brains (personal communication, Lary Walker, Yerkes Primate Center, Atlanta). Panels G and H: Thio-S staining of brain from control and 408-APP (neuronal expression) flies. The brains from >10 flies were examined in each analysis and the defects observed with EM were present in all examined brains. No such pathology was seen in control. The ThioS deposits were also examined in >10 brains and the difference between control and test flies were profound (see panels G and H; with almost no deposits in control and large number of deposits with neuronal APP expression).

FIG. 7. Illustration of multiple protease cut sites potentially producing one or more pathogenic peptide.

FIG. 9. APP-12-100 aa peptide. Marker peptide produced by the APP 12-100 aa peptide transgenic line. C is control, APP-Glia is full length APP expressed in glia producing the marker peptide, APP-12-100 is the transgenic line expressing the APP-12-100 peptide, producing the same marker peptide. MP, marker peptide.

FIG. 10. APP-12-94 aa peptide.

FIG. 14. Generation of a Marker Peptide-specific antibody. The inventors used a peptide of the following sequence to generate the antibody: DAE-FRHDSGYEVHHQKL (SEQ ID NO:18). Panel A: The commercial antibody that recognizes the marker peptide (IMG antibody). This antibody also recognizes many other bands, limiting its usefulness. Panels B and C: Our two separate antibodies against the peptide using the above sequence. The marker peptide band is weak, but this is a first bleed after immunization and the antibody appears to be much more specific than the commercial one (IMG Ab in panel A).

DESCRIPTION

Figure 11:
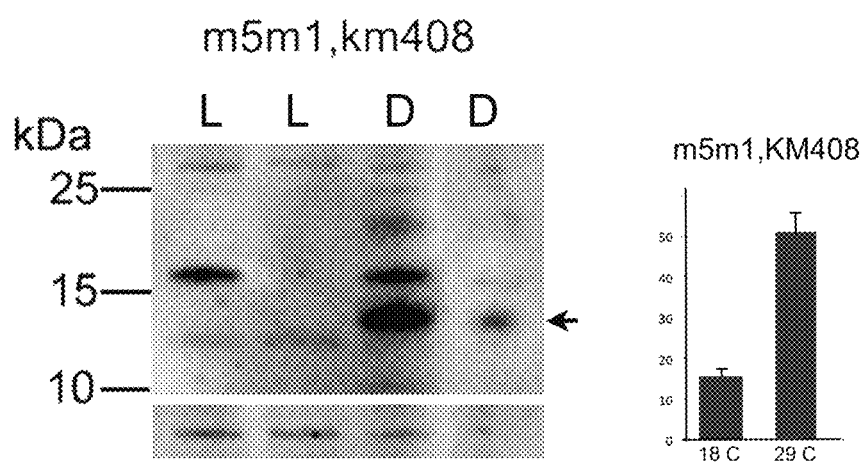
FIG. 11. Expression of 12-130 peptide (contains the marker peptide) in neurons of transgenic animals. L is living, D is diseased-dying. The presence of the marker peptide (arrow) correlates with the disease. The accompanying histogram shows the lethality of transgenic animals at two different temperatures; while normal flies live for about 100 days at 18 C and 50 days at 29 C (approximately), the transgenic flies start to develop the disease within two weeks with as many as 50% of the flies dying 29 C.
Figure 12:
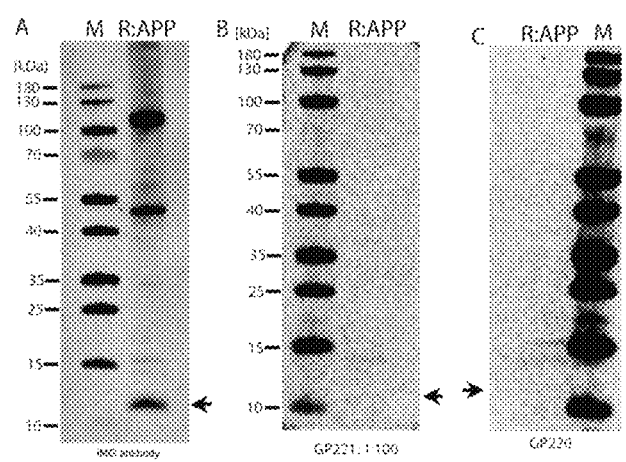
Figure 13:
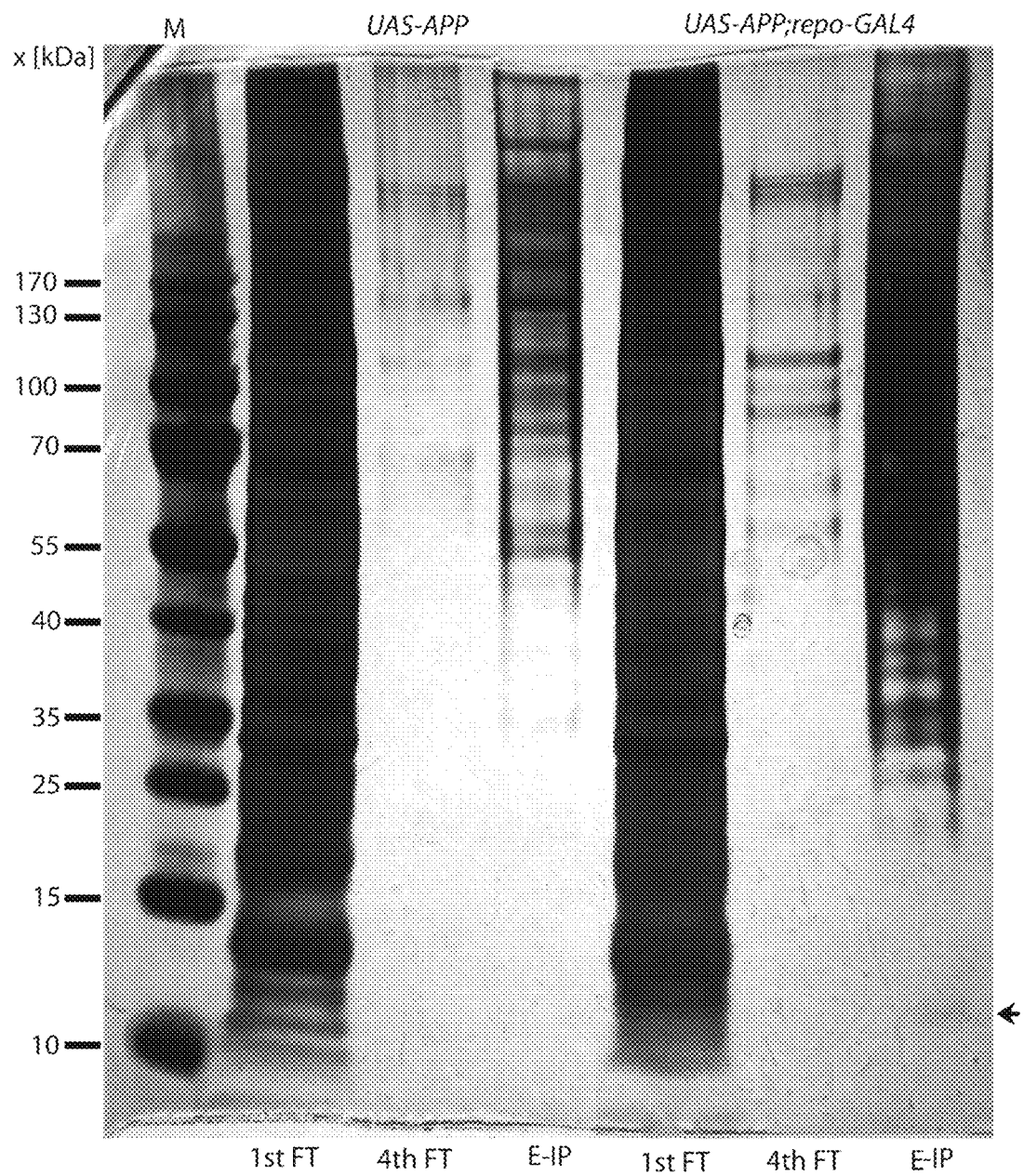
FIG. 13. Immunoprecipitation of the marker peptide using the IMG Ab. Immunoprecipitation and detection of the marker peptide: Brain samples from control and Alzheimer flies were prepared and subjected to immunoprecipitation (IP) in a column by an antibody that detects the ~12 kDa marker peptide. Following the IP, the flowthrough (FT) and IP-specific eluent were run on a polyacrylamide gel. M-molecular weight marker; UAS-APP—control non-Alzheimer flies; UAS-APP-repo-GAL—Alzheimer flies. $1^{st}$ FT—first flow-through washing from the antigen-antibody binding column, $4^{th}$ FT is the fourth flow through washing of the column. Note the column generates no bands in the 12 kDa region by this fourth wash. E-IP—elution of the bound protein(s) to the antibody. Note the specific band at the 12 kDa region (arrow).

The inventor has identified a unique APP peptide that is associated with lethality and neuropathology of Alzheimer's disease (AD). Based on the current studies only those that have the disease have this peptide (see FIGS. 4A, 4B, 5, 6, and 13). This peptide(s) can be used to diagnose and/or treat AD. This marker peptide from APP is not C99 or C83, or or Abeta, and has not been described before. The peptide(s) described herein can by itself cause AD-like disease (FIG. 11). Thus, using the peptide(s) described herein as therapeutic targets will be beneficial treating AD and/or AD associated symptoms or causes.

Non-limiting examples of symptoms and/or causes of Alzheimer's disease include amyloid aggregation, increased amyloid secretion, increased amyloid production, neuritic plaques, loss of normal physiological functions of amyloid, hyperphosphorylation of tau, increased neurofibrillary tangles, increased toxic species of tau, increased levels of tau, neuro-inflammation, etc. Additional non-limiting examples of symptoms of Alzheimer's disease include decreased cognition, memory impairment, confusion, visual impairment, impairment of spatial recognition, reduced vocabulary, depression, changes in mood, etc.

I. Diagnostic Methods

Certain methods include diagnosis of Alzheimer's disease (AD). Furthermore, in some examples, methods can include treatments commonly used to treat a subject identified as having AD or related symptoms. Diagnostic aspects of the invention include marker peptides and/or antibodies that bind to marker peptides (marker peptide antibodies) via either sequence specific or conformation specific epitope(s). The present invention provides for AD therapeutics that can induce a specific immune response against marker peptides or provide passive immunity to such peptides via administering the antibody or an immuogen (e.g., peptide or DNA or RNA) intravenously and/or intrathecally.

In particular aspects, the marker peptides or marker peptide antibodies can be used in producing diagnostic kits or used in diagnostic methods. The antibodies and/or marker peptides described herein can be used in immunohistochemical and biochemical methods in combination with other well characterized antibodies for qualitative and quantitative analysis of marker peptide levels and/or localization in brain samples and CSF samples. The methods for detecting a binding reaction between a marker peptide and a marker peptide binding antibody can include, but are not limited to ELISA, radioimmunoassay (RIA), sandwich assay, western blotting, immunoprecipitation, immunohistochemical staining, immunofluorescence method, enzyme-substrate colorimetry, and antigen/antibody agglutination assay.

A marker peptide or marker peptide antibody can be fixed on a solid substrate. The substrate bound peptide or antibody can provide for the washing, separation, and/or detection processes. The solid substrate can be a synthetic resin, nitrocellulose, glass plate, metal plate, glass fiber, microspheres, and/or microbeads. Examples of synthetic resin include polyester, polyvinyl chloride, polystyrene, polypropylene, PVDF and nylon. N-hydroxy-sulfosuccinimide and 1-ethyl-3-(3-dimethylaminopropyl)-carbodiimide hydrochloride can be used to couple the peptide or antibody to the substrate or support. In certain aspects a sample obtained from a subject or patient is contacted with the marker peptide or marker peptide antibody fixed on a solid substrate. In certain aspects the sample can be diluted or processed before use.

II. Polypeptide Or Peptide Compositions

Certain embodiments are related to peptides, antibodies, and antibody fragments for use in various embodiments of the present invention. For example, antibodies generated to a peptide comprising a peptide having an amino acid sequence of SEQ ID NO:2, 4, 6, 8, or 10 can be used in identifying AD or AD related symptoms.

A. Peptide Compositions

In certain embodiments, all or part of the peptides or proteins of the invention can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide of the invention is inserted into an expression vector, transformed or transfected into an appropriate host cell and cultivated under conditions suitable for expression.

In a certain aspects, an immunogenic composition according to the invention comprises a peptide that has at least 85% identity, at least 90% identity, at least 95% identity, or at least 97-99% identity, including all values and ranges there between, to a peptide having a sequence of SEQ ID NO:2, 4, and/or 6. In certain aspects the peptide is about 12 kDa+/−4 kDa.

It will be understood that in certain instances amino acid and nucleic acid sequences may include additional residues, such as additional N- or C-terminal amino acids, or 5' or 3' sequences, respectively, and yet still be essentially as set forth in one of the sequences disclosed herein (e.g., SEQ ID NO:2, 4, 6, 8, and/or 10). The addition of terminal sequences particularly applies to nucleic acid sequences that may, for example, include various non-coding sequences flanking either of the 5' or 3' portions of the coding region, and peptides that have N-terminal leader or signal sequences.

The following is a discussion based upon changing of the amino acids of a protein or peptide to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules (e.g., antigenic determinants or epitopes). Since it is the interactive capacity and nature of a protein that defines that protein's biological functional activity, certain amino acid substitutions can be made in a protein or peptide sequence, and in its underlying DNA coding sequence, and nevertheless produce a protein or peptide with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

B. Antibodies

Certain embodiments of the invention are directed to antibodies that specifically bind a peptide having all or part of the amino acid sequence of SEQ ID NO:2, 4, 6, 8, 10, or 18. In certain aspects the invention is directed to mouse monoclonal antibodies that specifically bind a peptide having all or part of the amino acid sequence of SEQ ID NO:2, 4, 6, 8, 10, or 18 as well as humanized versions of these mouse monoclonal antibodies.

To generate antibodies an immunostimulatory amount of inoculum is administered to a mammal and the inoculated mammal is then maintained for a time sufficient for the antigenic composition to induce protective antibodies. The antibodies can be isolated to the extent desired by well-known techniques such as affinity chromatography (Harlow and Lane, 1988). Antibodies can include antiserum preparations from a variety of commonly used animals e.g., goats, primates, donkeys, swine, horses, guinea pigs, rats or man.

Inocula for polyclonal antibody production are typically prepared by dispersing the antigenic composition (e.g., a peptide having all or part of the amino acid sequence of SEQ ID NO:2, 4, and/or 6) in a physiologically tolerable diluent such as saline or other adjuvants suitable for human use to form an aqueous composition.

Typically, antibodies to the antigen(s) are subsequently collected from the sera of the host. The polyclonal antibody can be affinity purified against the antigen rendering it monospecific. An antigen composition of the present invention can be administered to a recipient who then acts as a source of antibodies, produced in response to challenge with an antigen composition comprising a peptide having all or part of the amino acid sequence of SEQ ID NO:2, 4, 6, 8, 10, or 18. In certain instances a subject thus treated could donate plasma from which an antibody would be obtained via conventional plasma fractionation methodology; or would donate antibody producing cells that could be cultured and used for production of antibodies in culture. In other aspects, the gene encoding the antibody can be cloned, and antibody produced by recombinant methods. The isolated antibody would be administered to the same or different subject in order to impart resistance against or treat AD or related condition or symptom. In order to produce polyclonal antibodies, a host, such as a rabbit or goat or human, is immunized with the antigen or antigen segment, generally with an adjuvant and, if necessary, coupled to a carrier.

In some cases, to produce monoclonal antibodies, hyperimmunization of an appropriate donor, generally a mouse, with the antigen is undertaken. Isolation of splenic antibody producing cells is then carried out. These cells are fused to a cell characterized by immortality, such as a myeloma cell, to provide a fused cell hybrid (hybridoma) which can be maintained in culture and which secretes the required monoclonal antibody. The cells are then cultured, in bulk, and the monoclonal antibodies harvested from the culture media for use. By definition, monoclonal antibodies are specific to a single epitope. Monoclonal antibodies often have lower affinity constants than polyclonal antibodies raised against similar antigens for this reason.

Monoclonal antibodies may also be produced ex vivo by use of primary cultures of splenic cells or cell lines derived from spleen (Anavi, 1998). In order to produce recombinant antibody (see generally Huston et al., 1991; Johnson et al., 1991), messenger RNAs from antibody producing B-lymphocytes of animals, or hybridoma are reverse-transcribed to obtain complementary DNAs (cDNAs). Antibody cDNA, which can be full length or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries. Alternatively, monoclonal Fv fragments can be obtained by screening a suitable phage display library (Vaughan et al., 1998). Monoclonal antibodies may be human, humanized, or partially humanized by known methods.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Typically, antibodies are comprised of four polypeptide chains, two heavy (H) chains and two light (L) chains. In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyterminus in the following order: FRI, CDRI, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgAI and IgA2) or subclass.

The framework and CDR regions of an antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences.

III. Administration and Formulation

One use of compositions of the invention is to prophylactically treat a subject in early stages of AD by inoculating a subject with a marker peptide or marker peptide antibody, or a single stranded RNA (RNAi) or a DNA-vaccine (mon or multicistronic), particularly once a risk of developing AD has been indicated. In certain aspects, a "risk" means symptoms being presented or having a familial history of AD, i.e., a genetic predisposition.

The compositions and related methods of the present invention, particularly administration of an immunogenic composition comprising a peptide comprising, consisting of, or consisting essentially of all or part of an amino acid sequence of SEQ ID NO:2, 4, 6, 8, 10, or 18, or an antibody that specifically binds such a peptide to a patient/subject, may also be used in combination with the administration of traditional therapies.

In one aspect, it is contemplated that a traditional therapy is used in conjunction with a composition comprising a peptide comprising or consisting of an amino acid sequence of SEQ ID NO:2, 4, 6, 8, 10, and/or 18, or a marker peptide specific antibody or RNA/DNA treatment. Alternatively, the therapy may precede or follow the traditional therapy by intervals ranging from minutes to weeks. In embodiments where the other agents and/or a proteins or polynucleotides are administered separately, one would generally ensure that a significant period of time did not expire between the time of each delivery, such that the therapeutic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, where several days (2, 3, 4, 5, 6 or 7) to several weeks (1, 2, 3, 4, 5, 6, 7 or 8) lapse between the respective administrations.

Various combinations of therapy may be employed, for example, using immunogenic compositions or antibody therapy as a first therapeutic agent and an RNA/DNA agent or and a traditional AD therapy as additional therapeutic agents. The two or more therapeutic agents can be co-formulated, or they can be separately formulated and co-administered simultaneously or consecutively in any order. Therapeutics that restore the deficit (defect), or malfunctioning, in the chemical messengers of the nerve cells (neurotransmitters), in particular the cholinesterase inhibitors (ChEIs) such as tacrine and rivastigmine, have been shown to improve symptoms of AD. ChEIs impede the enzymatic degradation of neurotransmitters thereby increasing the amount of chemical messengers available to transmit the nerve signals in the brain.

In certain aspects, antibodies of the invention can be used to detect the effects of small molecules on the persistence or diminution of marker peptides in high-through put screening assays.

Compositions of the invention can be used to characterize marker peptides in human brain, serum, CSF, and transgenic animals.

Certain aspects in the use of the marker peptides as antigen include a vaccine specifically targeting toxic marker peptide (traditional vaccines or DNA vaccine). Furthermore, the marker peptide antibodies can be provided as a passive immunotherapy, intrabodies, humanized mAb agents for the detection and/or treatment of AD.

Marker peptides and marker peptide antibodies can be used in transgenic animal models for assessment of therapeutic efficacy. For example, marker peptides can be studied in brain from the AD models Tg 2576 and APP/PS1 mice, as well as the P301L amyloid (JNPL3) mice or APP-Glia or APP-neurons flies.

As discussed above, compositions can be administered to a subject having, suspected of having, or at risk of developing AD. Therapeutic compositions are administered in a manner compatible with the dosage formulation, and in such amount as will be therapeutically effective. The quantity to be administered depends on the subject to be treated. Precise amounts of active ingredient to be administered depend on the judgment of the practitioner. Suitable regimes for initial administration and boosters are also variable, but are typified by an initial administration followed by subsequent administrations.

The manner of application may be varied widely. Any of the conventional methods for administration of a peptide or a given treatment as a therapeutic are applicable. These are believed to include oral application on a solid physiologically acceptable base or in a physiologically acceptable dispersion, parenterally, intrathecally, dermally or by injection and the like. The dosage of the composition will depend on the route of administration and will vary according to the size and health of the subject. Administration of the compositions according to the present invention will typically be via any common route. This includes, but is not limited to oral, nasal, intrathecal, or buccal administration. Alternatively, administration may be by orthotopic, intradermal, subcutaneous, intramuscular, intraperitoneal, intranasal, or intravenous injection. In certain aspects a marker peptide specific antibody that specifically binds a peptide having all or part of the amino acid sequence of SEQ ID NO:2, 4, or 6 can be administered into the cerebrospinal fluid of the brain or spine. Such compositions would normally be administered as pharmaceutically acceptable compositions that include physiologically acceptable carriers, buffers or other excipients.

Administration of an antibody or immunogenic composition of the present invention to a patient/subject will follow general protocols for the administration of such compositions, taking into account the toxicity, if any, of the composition. It is expected that the treatment cycles would be repeated as necessary. It is also contemplated that various standard therapies, such as hydration, may be applied in combination with the described therapy. In some embodiments, an expression vector encoding one or more such antibodies or polypeptides or peptides may be given to a patient as a treatment. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as anti-infective agents and vaccines, can also be incorporated into the compositions.

A pharmaceutical composition comprising antibodies that specifically bind a marker peptide having an amino acid sequence of SEQ ID NO:2, 4, 6, 8, 10, or 18 and a pharmaceutically acceptable carrier is a further aspect of the invention that can be used in the manufacture of a medicament for the treatment or prevention of AD.

It is contemplated that in compositions of the invention, there is about 0.001, 0.01, 0.1, 1, 5, µg or mg to about 0.01, 0.1, 1, 5, 10 µg or mg of total polypeptide, peptide, and/or protein per ml. The concentration of protein in a composition can be about, at least about or at most about 0.001, 0.01, 0.05, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml, including all values and ranges there between. In certain aspects the dose range is 0.01 to 500 mg/kg, 10 to 300 mg/kg, or 0.01 to 10 mg/kg. About, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be a peptide having the amino acid sequence of SEQ ID NO:2, 4, or 6 or antibody that specifically binds the same.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

EXAMPLES

The following examples are included to demonstrate preferred embodiments of the invention. It should be appreciated by those of skill in the art that the techniques disclosed in the examples represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 1:
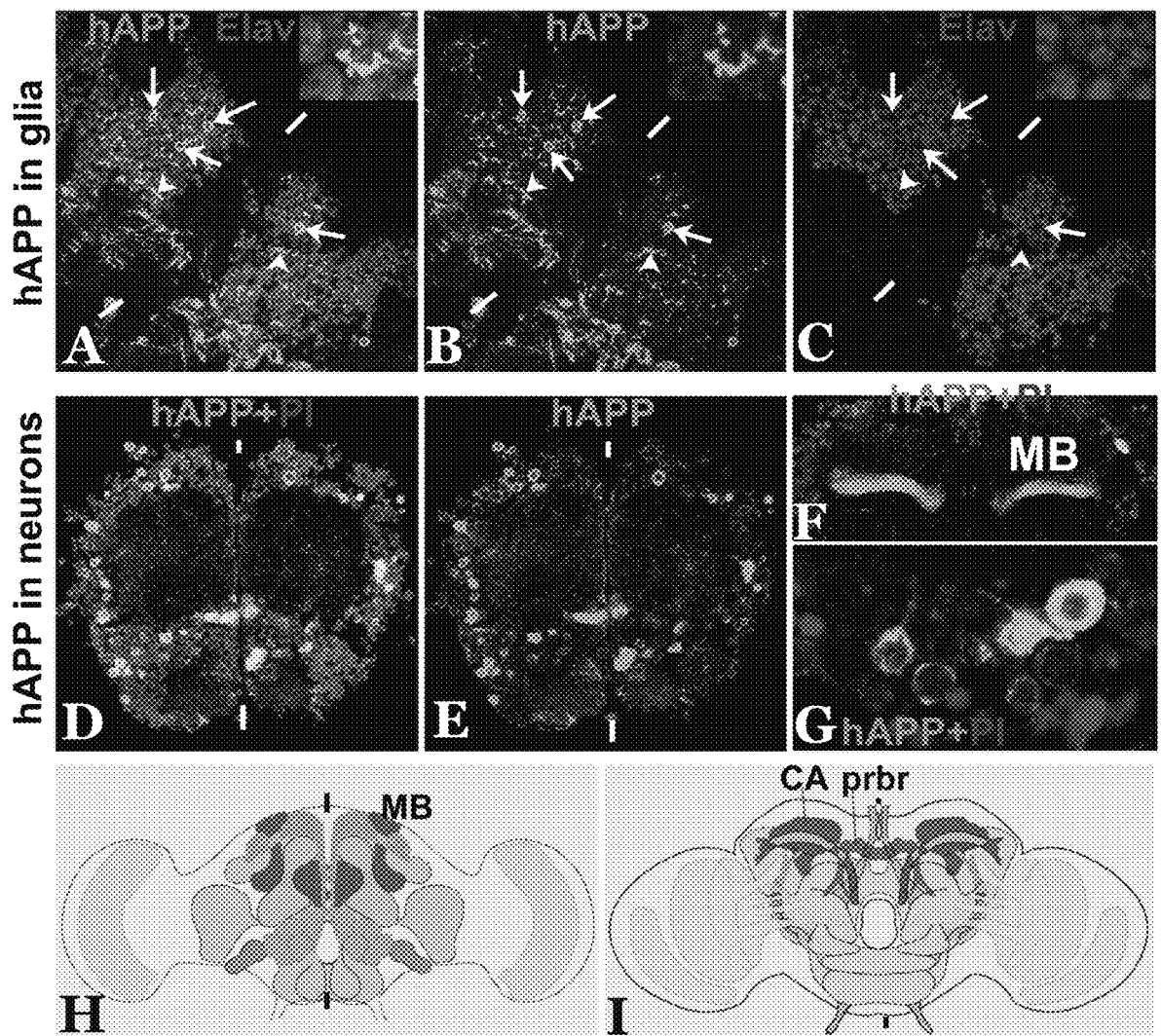
FIGS. 1A-I. Human APP localization in glia and neurons. APP was induced from UAS-APP with repo-GAL4 (A-C: APP in glial cells) and with 408-GAL4 (D-F: APP in neurons). Elav is used as a control stain for neurons in panels A-C which allows identification of glia by negative Elav staining, and propidium iodide is used to stain nuclear DNA stain for all cells in D-F. APP when induced in glia (A-C) is present in glial cell membranes and also intercellular spaces (see the inset figures, top right corner, A-C) but not in neurons. APP when induced in neurons (D-G) is present in neuronal membrane, axon tracts and synaptic terminals. No staining was observed in the brain of uninduced control (data not shown). Panels H and I show the major regions of the adult brain, CA, calyx of Mushroon Body (MB), prbr, protocerebral bridge. Vertical lines mark the left and the right brain hemispheres.
Figure 2:
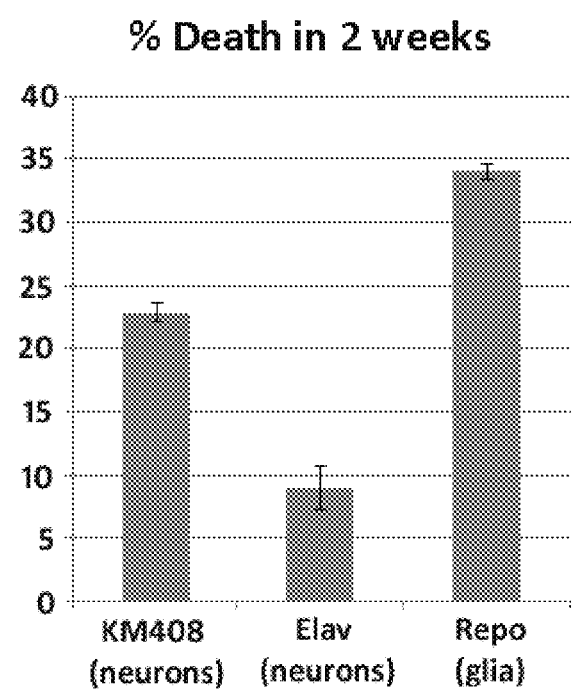
FIG. 2. Percentage of deaths in two weeks period with the expression of APP in neurons (drivers: KM408 and Elav), and in glia (driver: Repo). About 200 flies were examined for each experiment and the experiments were repeated 4 times. The values plotted were from these four separate experiments. The difference in lethality between neuronal versus glial expression was highly significant with p value 0.001 using the student t test.

Identification of Disease Causing Peptide of Human APP Expressed in *Drosophila* and Mouse The human APP gene was expressed in the fruit fly *Drosophila* adult brain, which resulted in the expression of APP protein in neurons and glial cells (see FIG. 1). As shown in FIG. 2, expression of the full length human APP either in the glial cells or in neurons in the adult fly brain causes neuropathology and lethality in flies, similar to AD in vertebrates (FIG. 3). Upon investigation of the cause for the lethality and neuropathology, it was found that the disease strictly correlated with the presence of a 12-14 kilo Dalton (kDa) peptide, processed from APP (FIGS. 4A, 4B, 6, and 13) (The molecular mass of this peptide varies between 12-14 kDa depending upon the gel conditions—this type of variability is not specific to this peptide, but also seen for other peptides and proteins).

Briefly, EM analysis was performed on the brain from flies expressing APP in neurons just before they died. The brain from these flies had striking neuropathologies such as structures that resemble the abnormal organelles/inclusions in dystrophic neurites, which are neuronal processes surrounding senile plaques in AD and in Aβ seeded APP/PS1 mice (Personal communication, Larry Walker, Yerkes Primate center, Atlanta)(FIG. 3F). These brains also had lamellar inclusions (arrow, FIG. 3B), found in mice models of AD as well. Additionally, there were holes with degenerating neurons (star, FIG. 3B-3D). The inventor further examined brains with Thioflavin S staining and found significant Thio-S positive deposits (FIG. 3G-3H). These defects correlate tightly with the disease severity/lethality. A fly that appeared normal had none to very little of these pathologies, whereas a fly that appeared to be very sick/dying always had these neuropathologies (when dying, these flies lay on their side for half a day or so, still alive).

Figure 4A:
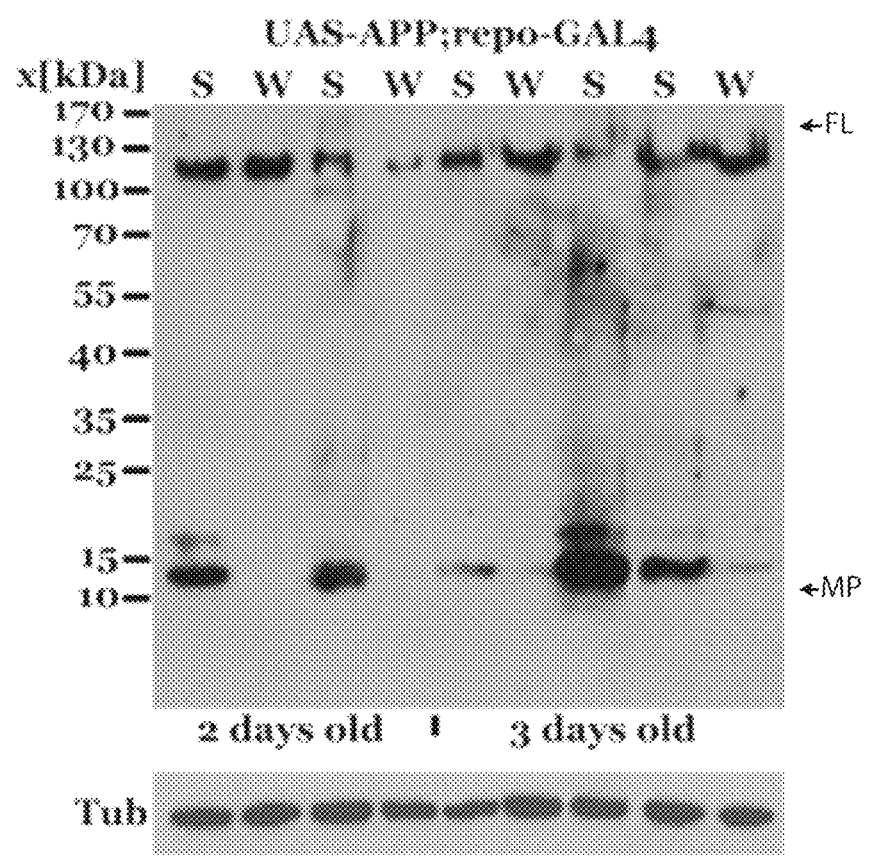
FIGS. 4A-B. Association between lethality and the 12 kDa fragment. Western analysis of brain extracts from APP expressing flies (glia and neurons) that were very sick (S) or behaviorally well (W) were performed. Note that the 12 kDa fragment is present at high levels only in sick and dying flies. The results were the same with glial and neuronal expression of APP.
Figure 4B:
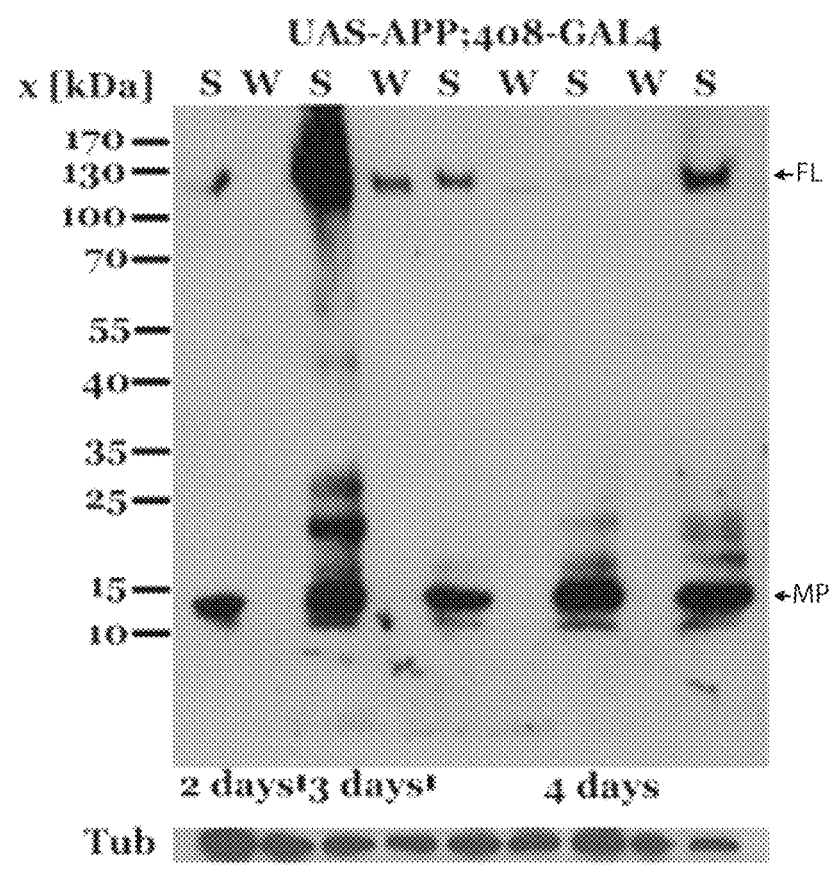

Western blots of brain extracts derived from flies that were sick and dying were compared to brain extracts from "well" flies from among the population where the full length human APP was induced in the brain. As shown in FIGS. 4A and 4B, a strict association between sickness and death and the presence of the 12-kDa marker peptide was observed. Given that the 12 kDa fragment is highly likely the common processed peptide in both glia and neurons, the inventor sought to determine if this fragment is associated with lethality. Brain extracts were prepared from flies that were "sick" (S; when they are on their side in the media with some limb movement, but not dead) and those not yet showing any obvious motor deficits (W) and examined the extracts by western analysis. As shown in FIGS. 4A and 4B, the 12 kDA fragment was associated with lethality. The dying flies always had this fragment. This indicates that this 12 kDa fragment is somehow involved in causing toxicity (and neuropathology).

Figure 5:
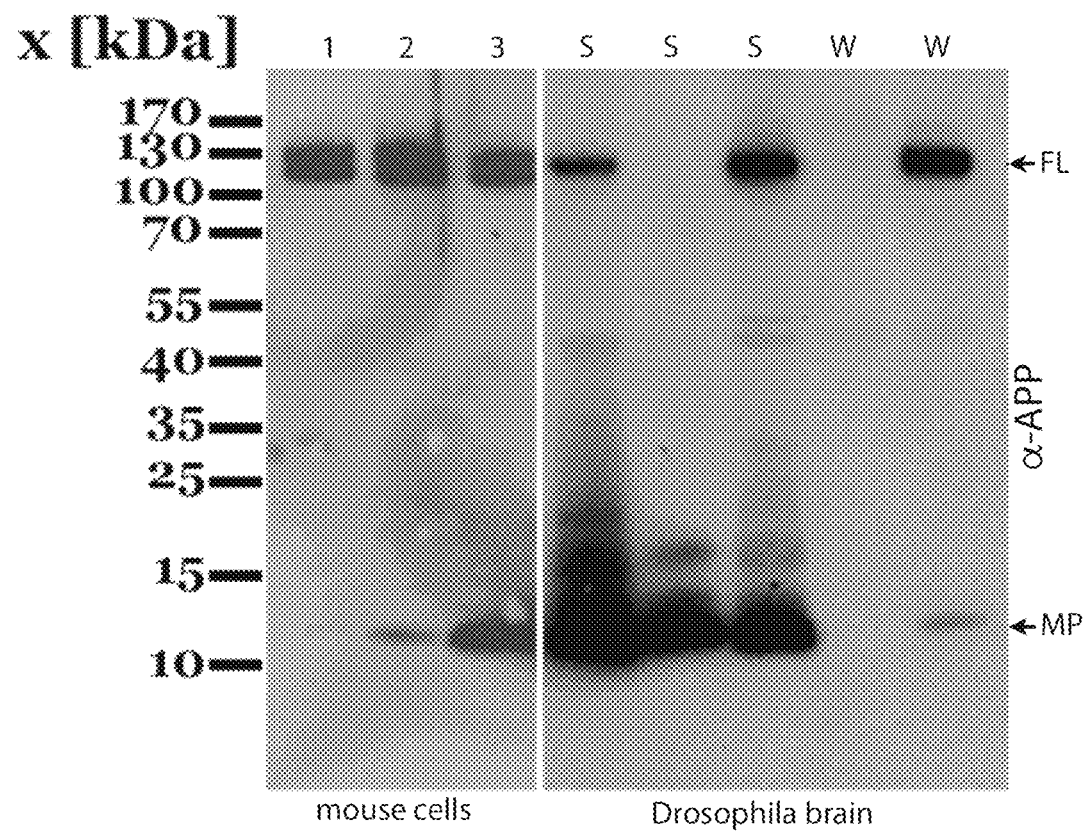
FIG. 5. Presence of the 12 kDa fragment in mouse cells and *Drosophila* brain. Mouse cell lines expressing various amounts of the full length APP were assessed. S, sick flies expressing the full length APP; W, well flies weakly expressing the full length APP.

As shown in FIG. 5, the 12-kDa marker peptide was also present in mouse cell lines expressing the full length APP at varying levels.

Example 2

Figure 6:
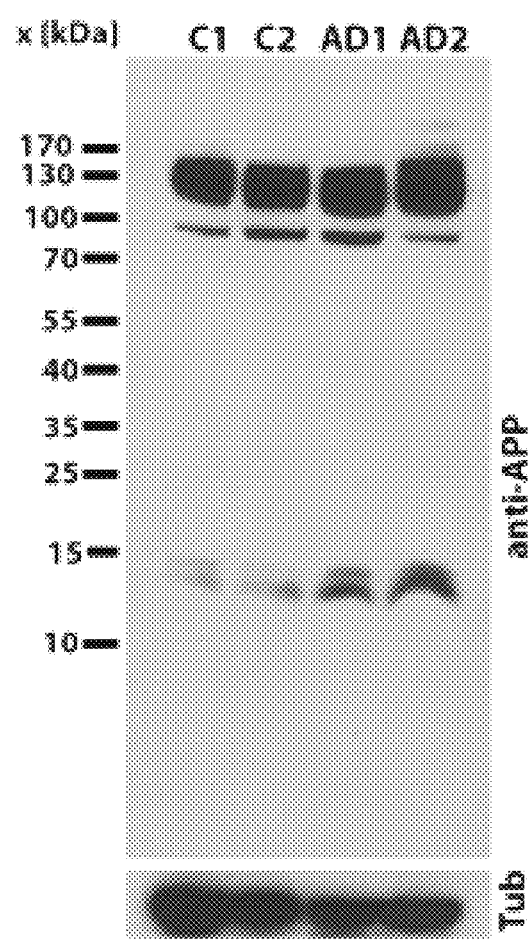
FIG. 6. Presence of the 12 kDa fragment in confirmed cases of Alzheimer's Disease. Human brain samples from control (C) and AD patients were evaluated. The controls had no neuropathology for AD but the AD patients had neuropathology that was confirmed by Electron microscopy. Tubulin (Tub) was used as loading control.

Identification of Disease Causing Peptide in Confirmed Cases of Alzheimer's Disease Next it was determined if the 12 kDa MP is present in human cases of the AD. The inventor obtained human brain samples from the AD brain bank center, UCSD, and performed EM for the neuropathology to independently confirm that the patients who contributed the brain samples indeed had AD. As shown in FIG. 6, human brain samples from confirmed cases of AD had elevated levels of the marker peptide.

Example 3

Identification of the Disease Causing Peptide

The inventor next sought to identify the exact amino acid composition of this marker peptide(s) using mass-spectroscopy. Peptides were immunoprecipitated from the brain extracts of flies expressing full length APP using an antibody that was raised against the first 10 amino acids of the C99/Aβ42 peptides. This antibody does not recognize C83, another peptide that has a similar molecular mass as the marker peptide (MP may be slightly larger). The Mass spec analysis revealed that the C terminal part of the MP maps to the end of the APP.

Given that the MP on a polyacrylamide gel appears to be slightly larger that C83 and same size as closer to the size of C99 peptides of APP, thus, it should be very similar or a little bit larger than C99. A peptide 119 amino acids counting from the C-terminus of APP was synthesized (FIG. 7A). This peptide was linked to the signal sequence derived from full length APP signal sequence (FIG. 7A).

Example 4

Disease Causing Peptide Causes Sickness and Lethality in Drosophila

Figure 8:
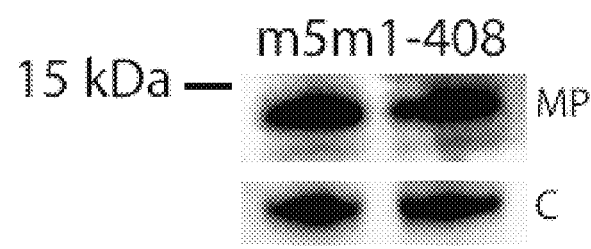
FIG. 8. The production of the 12-kDa peptide in diseased flies expressing a transgene expressing a marker peptide, as described herein. A 12-kDa peptide (MP) is produced in the above transgenic lines (the line shown here is m5m1) in neurons when the transgene was induced, which also cases lethality. C is the loading control, tubulin. The C-terminus of the peptide was determined by Mass-spectroscopy and mapped to the end of the protein.

The amino acid sequence that codes for the peptide sequence of FIG. 7A was cloned into a Drosophila transformation vector (pUAST) and Drosophila transgenic lines were generated. FIG. 8 shows that this transgenic line produced the 12 kDa marker peptide. APP is also processed into a C83 peptide, a C99 peptide, and A-Beta42 peptides. Transgenic lines were generated for each of these peptides as well by synthesizing the DNA fragments corresponding to these peptides along with the APP signal sequence (SEQ ID NO:15). Analysis of all these lines showed that only the 12 kDa MP expression caused sickness and lethality but none of the others (see also FIGS. 9 and 11). This suggests that this peptide is not only a marker for AD but also a therapeutic target. Accordingly, an interventional strategy against the disease can target this peptide.

The invention claimed is:

1. A method of detecting the presence of an APP (Amyloid Precursor Protein) Alzheimer's disease marker peptide in a patient with Alzheimer's disease, the method comprising: (a) obtaining a biological sample from a human subject with Alzheimer's disease; (b) isolating proteins from the biological sample; and (c) contacting the isolated proteins with a polyclonal antibody raised against an amino acid sequence consisting of the amino acid sequence of SEQ ID NO:18; and (d) identifying the APP Alzheimer's disease marker peptide as consisting of the amino acids: GLTTRPGSGLT-NIKTEEISEVKMDAEFRHDSGYEVHHQKLVFFAEDV GSNKGAIIGLMVGGVVIATVIVITLVMLKKKQYT SIHHGVVEVDAAVTPE ERHLSKMQQNGYENP-TYKFFEQMQN (SEQ ID NO:4) by mass spectrometry.

2. The method of claim 1, wherein isolating the proteins from the biological sample comprises size fractionating the proteins from the biological sample.

3. The method of claim 2, further comprising immunoprecipitating the biological sample with the polyclonal antibody prior to size fraction or detection.

4. The method of claim 2, wherein protein fractionation is by size exclusion chromatography or gel electrophoresis.

5. The method of claim 4, wherein protein fractionation is by denaturing polyacrylamide gel electrophoresis.

6. The method of claim 1, wherein the biological sample comprises plasma, cerebrospinal fluid (CSF), brain tissue, neuronal tissue, or muscle tissue.

7. The method of claim 1, wherein the polyclonal antibody comprises a detectable agent or label.

8. The method of claim 7, wherein the detectable agent is a radioactive marker, a fluorescent label, or an enzymatic label.

* * * * *

SEQUENCE LISTING

<160> NUMBER OF SEQ ID NOS: 19

<210> SEQ ID NO 1
<211> LENGTH: 390
<212> TYPE: DNA
<213> ORGANISM: Homo sapiens
<220> FEATURE:
<221> NAME/KEY: CDS
<222> LOCATION: (1)..(390)

<400> SEQUENCE: 1

| gat | gcc | cgc | cct | gct | gcc | gac | cga | gga | ctg | acc | act | cga | cca | ggt | tct | 48 |
| Asp | Ala | Arg | Pro | Ala | Ala | Asp | Arg | Gly | Leu | Thr | Thr | Arg | Pro | Gly | Ser | |
| 1 | | | | 5 | | | | | 10 | | | | | 15 | | |

| ggg | ttg | aca | aat | atc | aag | acg | gag | gag | atc | tct | gaa | gtg | aag | atg | gat | 96 |
| Gly | Leu | Thr | Asn | Ile | Lys | Thr | Glu | Glu | Ile | Ser | Glu | Val | Lys | Met | Asp | |
| | | | 20 | | | | | 25 | | | | | 30 | | | |

| gca | gaa | ttc | cga | cat | gac | tca | gga | tat | gaa | gtt | cat | cat | caa | aaa | ttg | 144 |
| Ala | Glu | Phe | Arg | His | Asp | Ser | Gly | Tyr | Glu | Val | His | His | Gln | Lys | Leu | |
| | | 35 | | | | | 40 | | | | | 45 | | | | |

| gtg | ttc | ttt | gca | gaa | gat | gtg | ggt | tca | aac | aaa | ggt | gca | atc | att | gga | 192 |
| Val | Phe | Phe | Ala | Glu | Asp | Val | Gly | Ser | Asn | Lys | Gly | Ala | Ile | Ile | Gly | |
| 50 | | | | | 55 | | | | | 60 | | | | | | |

| ctc | atg | gtg | ggc | ggt | gtt | gtc | ata | gcg | aca | gtg | atc | gtc | atc | acc | ttg | 240 |
| Leu | Met | Val | Gly | Gly | Val | Val | Ile | Ala | Thr | Val | Ile | Val | Ile | Thr | Leu | |
| 65 | | | | | 70 | | | | | 75 | | | | | 80 | |

| gtg | atg | ctg | aag | aag | aaa | cag | tac | aca | tcc | att | cat | cat | ggt | gtg | gtg | 288 |
| Val | Met | Leu | Lys | Lys | Lys | Gln | Tyr | Thr | Ser | Ile | His | His | Gly | Val | Val | |
| | | | | 85 | | | | | 90 | | | | | 95 | | |

| gag | gtt | gac | gcc | gct | gtc | acc | cca | gag | gag | cgc | cac | ctg | tcc | aag | atg | 336 |
| Glu | Val | Asp | Ala | Ala | Val | Thr | Pro | Glu | Glu | Arg | His | Leu | Ser | Lys | Met | |
| | | | 100 | | | | | 105 | | | | | 110 | | | |

| cag | cag | aac | ggc | tac | gaa | aat | cca | acc | tac | aag | ttc | ttt | gag | cag | atg | 384 |
| Gln | Gln | Asn | Gly | Tyr | Glu | Asn | Pro | Thr | Tyr | Lys | Phe | Phe | Glu | Gln | Met | |
| | | 115 | | | | | 120 | | | | | 125 | | | | |

| cag | aac | | | | | | | | | | | | | | | 390 |
| Gln | Asn | | | | | | | | | | | | | | | |
| | 130 | | | | | | | | | | | | | | | |

<210> SEQ ID NO 2
<211> LENGTH: 130
<212> TYPE: PRT
<213> ORGANISM: Homo sapiens

<400> SEQUENCE: 2

| Asp | Ala | Arg | Pro | Ala | Ala | Asp | Arg | Gly | Leu | Thr | Thr | Arg | Pro | Gly | Ser |
| 1 | | | | 5 | | | | | 10 | | | | | 15 | |

| Gly | Leu | Thr | Asn | Ile | Lys | Thr | Glu | Glu | Ile | Ser | Glu | Val | Lys | Met | Asp |
| | | | 20 | | | | | 25 | | | | | 30 | | |

| Ala | Glu | Phe | Arg | His | Asp | Ser | Gly | Tyr | Glu | Val | His | His | Gln | Lys | Leu |
| | | 35 | | | | | 40 | | | | | 45 | | | |

| Val | Phe | Phe | Ala | Glu | Asp | Val | Gly | Ser | Asn | Lys | Gly | Ala | Ile | Ile | Gly |
| 50 | | | | | 55 | | | | | 60 | | | | | |

| Leu | Met | Val | Gly | Gly | Val | Val | Ile | Ala | Thr | Val | Ile | Val | Ile | Thr | Leu |
| 65 | | | | | 70 | | | | | 75 | | | | | 80 |

| Val | Met | Leu | Lys | Lys | Lys | Gln | Tyr | Thr | Ser | Ile | His | His | Gly | Val | Val |
| | | | | 85 | | | | | 90 | | | | | 95 | |

| Glu | Val | Asp | Ala | Ala | Val | Thr | Pro | Glu | Glu | Arg | His | Leu | Ser | Lys | Met |
| | | | 100 | | | | | 105 | | | | | 110 | | |

| Gln | Gln | Asn | Gly | Tyr | Glu | Asn | Pro | Thr | Tyr | Lys | Phe | Phe | Glu | Gln | Met |
| | | 115 | | | | | 120 | | | | | 125 | | | |

| Gln | Asn |
| | 130 |

<210> SEQ ID NO 3
<211> LENGTH: 366
<212> TYPE: DNA
<213> ORGANISM: Homo sapiens

```
<220> FEATURE:
<221> NAME/KEY: CDS
<222> LOCATION: (1)..(366)

<400> SEQUENCE: 3 gga ctg acc act cga cca ggt tct ggg ttg aca aat atc aag acg gag      48
Gly Leu Thr Thr Arg Pro Gly Ser Gly Leu Thr Asn Ile Lys Thr Glu
1               5                   10                  15 gag atc tct gaa gtg aag atg gat gca gaa ttc cga cat gac tca gga      96
Glu Ile Ser Glu Val Lys Met Asp Ala Glu Phe Arg His Asp Ser Gly
            20                  25                  30 tat gaa gtt cat cat caa aaa ttg gtg ttc ttt gca gaa gat gtg ggt     144
Tyr Glu Val His His Gln Lys Leu Val Phe Phe Ala Glu Asp Val Gly
        35                  40                  45 tca aac aaa ggt gca atc att gga ctc atg gtg ggc ggt gtt gtc ata     192
Ser Asn Lys Gly Ala Ile Ile Gly Leu Met Val Gly Gly Val Val Ile
    50                  55                  60 gcg aca gtg atc gtc atc acc ttg gtg atg ctg aag aag aaa cag tac     240
Ala Thr Val Ile Val Ile Thr Leu Val Met Leu Lys Lys Lys Gln Tyr
65                  70                  75                  80 aca tcc att cat cat ggt gtg gtg gag gtt gac gcc gct gtc acc cca     288
Thr Ser Ile His His Gly Val Val Glu Val Asp Ala Ala Val Thr Pro
                85                  90                  95 gag gag cgc cac ctg tcc aag atg cag cag aac ggc tac gaa aat cca     336
Glu Glu Arg His Leu Ser Lys Met Gln Gln Asn Gly Tyr Glu Asn Pro
            100                 105                 110 acc tac aag ttc ttt gag cag atg cag aac                             366
Thr Tyr Lys Phe Phe Glu Gln Met Gln Asn
        115                 120

<210> SEQ ID NO 4
<211> LENGTH: 122
<212> TYPE: PRT
<213> ORGANISM: Homo sapiens

<400> SEQUENCE: 4

Gly Leu Thr Thr Arg Pro Gly Ser Gly Leu Thr Asn Ile Lys Thr Glu
1               5                   10                  15

Glu Ile Ser Glu Val Lys Met Asp Ala Glu Phe Arg His Asp Ser Gly
            20                  25                  30

Tyr Glu Val His His Gln Lys Leu Val Phe Phe Ala Glu Asp Val Gly
        35                  40                  45

Ser Asn Lys Gly Ala Ile Ile Gly Leu Met Val Gly Gly Val Val Ile
    50                  55                  60

Ala Thr Val Ile Val Ile Thr Leu Val Met Leu Lys Lys Lys Gln Tyr
65                  70                  75                  80

Thr Ser Ile His His Gly Val Val Glu Val Asp Ala Ala Val Thr Pro
                85                  90                  95

Glu Glu Arg His Leu Ser Lys Met Gln Gln Asn Gly Tyr Glu Asn Pro
            100                 105                 110

Thr Tyr Lys Phe Phe Glu Gln Met Gln Asn
        115                 120

<210> SEQ ID NO 5
<211> LENGTH: 324
<212> TYPE: DNA
<213> ORGANISM: Homo sapiens
<220> FEATURE:
<221> NAME/KEY: CDS
<222> LOCATION: (1)..(324)
```

<400> SEQUENCE: 5

```
acg gag gag atc tct gaa gtg aag atg gat gca gaa ttc cga cat gac      48
Thr Glu Glu Ile Ser Glu Val Lys Met Asp Ala Glu Phe Arg His Asp
1               5                   10                  15 tca gga tat gaa gtt cat cat caa aaa ttg gtg ttc ttt gca gaa gat      96
Ser Gly Tyr Glu Val His His Gln Lys Leu Val Phe Phe Ala Glu Asp
            20                  25                  30 gtg ggt tca aac aaa ggt gca atc att gga ctc atg gtg ggc ggt gtt     144
Val Gly Ser Asn Lys Gly Ala Ile Ile Gly Leu Met Val Gly Gly Val
        35                  40                  45 gtc ata gcg aca gtg atc gtc atc acc ttg gtg atg ctg aag aag aaa     192
Val Ile Ala Thr Val Ile Val Ile Thr Leu Val Met Leu Lys Lys Lys
50                  55                  60 cag tac aca tcc att cat cat ggt gtg gtg gag gtt gac gcc gct gtc     240
Gln Tyr Thr Ser Ile His His Gly Val Val Glu Val Asp Ala Ala Val
65                  70                  75                  80 acc cca gag gag cgc cac ctg tcc aag atg cag cag aac ggc tac gaa     288
Thr Pro Glu Glu Arg His Leu Ser Lys Met Gln Gln Asn Gly Tyr Glu
                85                  90                  95 aat cca acc tac aag ttc ttt gag cag atg cag aac                     324
Asn Pro Thr Tyr Lys Phe Phe Glu Gln Met Gln Asn
            100                 105
```

<210> SEQ ID NO 6
<211> LENGTH: 108
<212> TYPE: PRT
<213> ORGANISM: Homo sapiens

<400> SEQUENCE: 6

```
Thr Glu Glu Ile Ser Glu Val Lys Met Asp Ala Glu Phe Arg His Asp
1               5                   10                  15

Ser Gly Tyr Glu Val His His Gln Lys Leu Val Phe Phe Ala Glu Asp
            20                  25                  30

Val Gly Ser Asn Lys Gly Ala Ile Ile Gly Leu Met Val Gly Gly Val
        35                  40                  45

Val Ile Ala Thr Val Ile Val Ile Thr Leu Val Met Leu Lys Lys Lys
50                  55                  60

Gln Tyr Thr Ser Ile His His Gly Val Val Glu Val Asp Ala Ala Val
65                  70                  75                  80

Thr Pro Glu Glu Arg His Leu Ser Lys Met Gln Gln Asn Gly Tyr Glu
                85                  90                  95

Asn Pro Thr Tyr Lys Phe Phe Glu Gln Met Gln Asn
            100                 105
```

<210> SEQ ID NO 7
<211> LENGTH: 360
<212> TYPE: DNA
<213> ORGANISM: Homo sapiens
<220> FEATURE:
<221> NAME/KEY: CDS
<222> LOCATION: (1)..(327)

<400> SEQUENCE: 7

```
acg gag gag atc tct gaa gtg aag atg gat gca gaa ttc cga cat gac      48
Thr Glu Glu Ile Ser Glu Val Lys Met Asp Ala Glu Phe Arg His Asp
1               5                   10                  15 tca gga tat gaa gtt cat cat caa aaa ttg gtg ttc ttt gca gaa gat      96
Ser Gly Tyr Glu Val His His Gln Lys Leu Val Phe Phe Ala Glu Asp
            20                  25                  30
```

-continued

```
gtg ggt tca aac aaa ggt gca atc att gga ctc atg gtg ggc ggt gtt      144
Val Gly Ser Asn Lys Gly Ala Ile Ile Gly Leu Met Val Gly Gly Val
         35                  40                  45 gtc ata gcg aca gtg atc gtc atc acc ttg gtg atg ctg aag aag aaa      192
Val Ile Ala Thr Val Ile Val Ile Thr Leu Val Met Leu Lys Lys Lys
 50                  55                  60 cag tac aca tcc att cat cat ggt gtg gtg gag gtt gac gcc gct gtc      240
Gln Tyr Thr Ser Ile His His Gly Val Val Glu Val Asp Ala Ala Val
 65                  70                  75                  80 acc cca gag gag cgc cac ctg tcc aag atg cag cag aac ggc tac gaa      288
Thr Pro Glu Glu Arg His Leu Ser Lys Met Gln Gln Asn Gly Tyr Glu
                 85                  90                  95 aat cca acc tac aag ttc ttt gag cag atg cag aac tag accccctagg      337
Asn Pro Thr Tyr Lys Phe Phe Glu Gln Met Gln Asn
                100                 105 ccacagctcg agcagcctct gaa                                            360

<210> SEQ ID NO 8
<211> LENGTH: 108
<212> TYPE: PRT
<213> ORGANISM: Homo sapiens

<400> SEQUENCE: 8

Thr Glu Glu Ile Ser Glu Val Lys Met Asp Ala Glu Phe Arg His Asp
 1               5                  10                  15

Ser Gly Tyr Glu Val His His Gln Lys Leu Val Phe Phe Ala Glu Asp
             20                  25                  30

Val Gly Ser Asn Lys Gly Ala Ile Ile Gly Leu Met Val Gly Gly Val
         35                  40                  45

Val Ile Ala Thr Val Ile Val Ile Thr Leu Val Met Leu Lys Lys Lys
 50                  55                  60

Gln Tyr Thr Ser Ile His His Gly Val Val Glu Val Asp Ala Ala Val
 65                  70                  75                  80

Thr Pro Glu Glu Arg His Leu Ser Lys Met Gln Gln Asn Gly Tyr Glu
                 85                  90                  95

Asn Pro Thr Tyr Lys Phe Phe Glu Gln Met Gln Asn
                100                 105

<210> SEQ ID NO 9
<211> LENGTH: 318
<212> TYPE: DNA
<213> ORGANISM: Homo sapiens
<220> FEATURE:
<221> NAME/KEY: CDS
<222> LOCATION: (1)..(282)

<400> SEQUENCE: 9 cat gac tca gga tat gaa gtt cat cat caa aaa ttg gtg ttc ttt gca      48
His Asp Ser Gly Tyr Glu Val His His Gln Lys Leu Val Phe Phe Ala
 1               5                  10                  15 gaa gat gtg ggt tca aac aaa ggt gca atc att gga ctc atg gtg ggc      96
Glu Asp Val Gly Ser Asn Lys Gly Ala Ile Ile Gly Leu Met Val Gly
             20                  25                  30 ggt gtt gtc ata gcg aca gtg atc gtc atc acc ttg gtg atg ctg aag      144
Gly Val Val Ile Ala Thr Val Ile Val Ile Thr Leu Val Met Leu Lys
         35                  40                  45 aag aaa cag tac aca tcc att cat cat ggt gtg gtg gag gtt gac gcc      192
Lys Lys Gln Tyr Thr Ser Ile His His Gly Val Val Glu Val Asp Ala
 50                  55                  60
```

```
gct gtc acc cca gag gag cgc cac ctg tcc aag atg cag cag aac ggc      240
Ala Val Thr Pro Glu Glu Arg His Leu Ser Lys Met Gln Gln Asn Gly
 65                  70                  75                  80 tac gaa aat cca acc tac aag ttc ttt gag cag atg cag aac              282
Tyr Glu Asn Pro Thr Tyr Lys Phe Phe Glu Gln Met Gln Asn
                 85                  90 tagaccccct aggccacagc tcgagcagcc tctgaa                              318
```

<210> SEQ ID NO 10
<211> LENGTH: 94
<212> TYPE: PRT
<213> ORGANISM: Homo sapiens

<400> SEQUENCE: 10

```
His Asp Ser Gly Tyr Glu Val His His Gln Lys Leu Val Phe Phe Ala
 1               5                  10                  15

Glu Asp Val Gly Ser Asn Lys Gly Ala Ile Ile Gly Leu Met Val Gly
                 20                  25                  30

Gly Val Val Ile Ala Thr Val Ile Val Ile Thr Leu Val Met Leu Lys
                 35                  40                  45

Lys Lys Gln Tyr Thr Ser Ile His His Gly Val Val Glu Val Asp Ala
 50                  55                  60

Ala Val Thr Pro Glu Glu Arg His Leu Ser Lys Met Gln Gln Asn Gly
 65                  70                  75                  80

Tyr Glu Asn Pro Thr Tyr Lys Phe Phe Glu Gln Met Gln Asn
                 85                  90
```

<210> SEQ ID NO 11
<211> LENGTH: 563
<212> TYPE: DNA
<213> ORGANISM: Homo sapiens
<220> FEATURE:
<221> NAME/KEY: CDS
<222> LOCATION: (3)..(530)

<400> SEQUENCE: 11

```
gc aaa gag gag cag cgg ccg caa aac atg ctg ccc ggt ttg gca ctg       47
   Lys Glu Glu Gln Arg Pro Gln Asn Met Leu Pro Gly Leu Ala Leu
    1               5                  10                  15 ctc ctg ctg gcc gcc tgg acg gct cgg gcg aca cac ctc cgt gtg att      95
Leu Leu Leu Ala Ala Trp Thr Ala Arg Ala Thr His Leu Arg Val Ile
                 20                  25                  30 tat gag cgc atg aat cag tct ctc tcc ctg ctc tac aac gtg cct gca     143
Tyr Glu Arg Met Asn Gln Ser Leu Ser Leu Leu Tyr Asn Val Pro Ala
                 35                  40                  45 gtg gcc gag gag att cag gat gaa gtt gat gag ctg ctt cag aaa gag     191
Val Ala Glu Glu Ile Gln Asp Glu Val Asp Glu Leu Leu Gln Lys Glu
 50                  55                  60 caa aac tat tca gat gac gtc ttg gcc aac atg att agt gaa cca agg     239
Gln Asn Tyr Ser Asp Asp Val Leu Ala Asn Met Ile Ser Glu Pro Arg
 65                  70                  75 atc agt tac gga aac gat gct ctc atg cca tct ttg acc gaa acg aaa     287
Ile Ser Tyr Gly Asn Asp Ala Leu Met Pro Ser Leu Thr Glu Thr Lys
 80                  85                  90                  95 acc acc gtg gag ctc ctt ccc gtg aat gga gag ttc agc ctg gac gat     335
Thr Thr Val Glu Leu Leu Pro Val Asn Gly Glu Phe Ser Leu Asp Asp
                100                 105                 110 ctc cag ccg tgg cat tct ttt ggg gct gac tct gtg cca gcc aac aca     383
Leu Gln Pro Trp His Ser Phe Gly Ala Asp Ser Val Pro Ala Asn Thr
                115                 120                 125
```

```
gaa aac gaa gtt gag cct gtt gat gcc cgc cct gct gcc gac cga gga      431
Glu Asn Glu Val Glu Pro Val Asp Ala Arg Pro Ala Ala Asp Arg Gly
    130                 135                 140 ctg acc act cga cca ggt tct ggg ttg aca aat atc aag acg gag gag      479
Leu Thr Thr Arg Pro Gly Ser Gly Leu Thr Asn Ile Lys Thr Glu Glu
145                 150                 155 atc tct gaa gtg aag atg gat gca gaa ttc cga cat gac tca gga tat      527
Ile Ser Glu Val Lys Met Asp Ala Glu Phe Arg His Asp Ser Gly Tyr
160                 165                 170                 175 tag acccctagg ccacagctcg agcagcctct gaa                              563
```

<210> SEQ ID NO 12
<211> LENGTH: 175
<212> TYPE: PRT
<213> ORGANISM: Homo sapiens

<400> SEQUENCE: 12

```
Lys Glu Glu Gln Arg Pro Gln Asn Met Leu Pro Gly Leu Ala Leu Leu
1               5                   10                  15

Leu Leu Ala Ala Trp Thr Ala Arg Ala Thr His Leu Arg Val Ile Tyr
                20                  25                  30

Glu Arg Met Asn Gln Ser Leu Ser Leu Leu Tyr Asn Val Pro Ala Val
            35                  40                  45

Ala Glu Glu Ile Gln Asp Glu Val Asp Glu Leu Leu Gln Lys Glu Gln
        50                  55                  60

Asn Tyr Ser Asp Asp Val Leu Ala Asn Met Ile Ser Glu Pro Arg Ile
65                  70                  75                  80

Ser Tyr Gly Asn Asp Ala Leu Met Pro Ser Leu Thr Glu Thr Lys Thr
                85                  90                  95

Thr Val Glu Leu Leu Pro Val Asn Gly Glu Phe Ser Leu Asp Asp Leu
            100                 105                 110

Gln Pro Trp His Ser Phe Gly Ala Asp Ser Val Pro Ala Asn Thr Glu
        115                 120                 125

Asn Glu Val Glu Pro Val Asp Ala Arg Pro Ala Ala Asp Arg Gly Leu
    130                 135                 140

Thr Thr Arg Pro Gly Ser Gly Leu Thr Asn Ile Lys Thr Glu Glu Ile
145                 150                 155                 160

Ser Glu Val Lys Met Asp Ala Glu Phe Arg His Asp Ser Gly Tyr
                165                 170                 175
```

<210> SEQ ID NO 13
<211> LENGTH: 155
<212> TYPE: PRT
<213> ORGANISM: Homo sapiens

<400> SEQUENCE: 13

```
Lys Glu Glu Gln Arg Pro Gln Asn Met Leu Pro Gly Leu Ala Leu Leu
1               5                   10                  15

Leu Leu Ala Ala Trp Thr Ala Arg Ala Asp Ala Arg Pro Ala Ala Asp
                20                  25                  30

Arg Gly Leu Thr Thr Arg Pro Gly Ser Gly Leu Thr Asn Ile Lys Thr
            35                  40                  45

Glu Glu Ile Ser Glu Val Lys Met Asp Ala Glu Phe Arg His Asp Ser
        50                  55                  60

Gly Tyr Glu Val His His Gln Lys Leu Val Phe Ala Glu Asp Val
65                  70                  75                  80
```

```
Gly Ser Asn Lys Gly Ala Ile Ile Gly Leu Met Val Gly Gly Val Val
                85                  90                  95

Ile Ala Thr Val Ile Val Ile Thr Leu Val Met Leu Lys Lys Lys Gln
            100                 105                 110

Tyr Thr Ser Ile His His Gly Val Val Glu Val Asp Ala Ala Val Thr
        115                 120                 125

Pro Glu Glu Arg His Leu Ser Lys Met Gln Gln Asn Gly Tyr Glu Asn
    130                 135                 140

Pro Thr Tyr Lys Phe Phe Glu Gln Met Gln Asn
145                 150                 155

<210> SEQ ID NO 14
<211> LENGTH: 25
<212> TYPE: PRT
<213> ORGANISM: Homo sapiens

<400> SEQUENCE: 14

Lys Glu Glu Gln Arg Pro Gln Asn Met Leu Pro Gly Leu Ala Leu Leu
1               5                   10                  15

Leu Leu Ala Ala Trp Thr Ala Arg Ala
            20                  25

<210> SEQ ID NO 15
<211> LENGTH: 17
<212> TYPE: PRT
<213> ORGANISM: Homo sapiens

<400> SEQUENCE: 15

Met Leu Pro Gly Leu Ala Leu Leu Leu Ala Ala Trp Thr Ala Arg
1               5                   10                  15

Ala

<210> SEQ ID NO 16
<211> LENGTH: 77
<212> TYPE: DNA
<213> ORGANISM: Homo sapiens

<400> SEQUENCE: 16
gcaaagagga gcagcggccg caaaacatgc tgcccggttt ggcactgctc ctgctggccg     60
cctggacggc tcgggcg                                                   77

<210> SEQ ID NO 17
<211> LENGTH: 36
<212> TYPE: DNA
<213> ORGANISM: Homo sapiens

<400> SEQUENCE: 17
tagaccccct aggccacagc tcgagcagcc tctgaa                              36

<210> SEQ ID NO 18
<211> LENGTH: 17
<212> TYPE: PRT
<213> ORGANISM: Homo sapiens

<400> SEQUENCE: 18

Asp Ala Glu Phe Arg His Asp Ser Gly Tyr Glu Val His His Gln Lys
1               5                   10                  15

Leu
```

<210> SEQ ID NO 19
<211> LENGTH: 770
<212> TYPE: PRT
<213> ORGANISM: Homo sapiens

<400> SEQUENCE: 19

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

-continued

```
Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Ala
            405                 410                 415

Glu Arg Gln Ala Lys Asn Leu Pro Lys Ala Asp Lys Lys Ala Val Ile
                420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
                500                 505                 510

Glu His Val Arg Met Val Asp Pro Lys Lys Ala Gln Ile Arg Ser
        515                 520                 525

Gln Val Met Thr His Leu Arg Val Ile Tyr Glu Arg Met Asn Gln Ser
530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
            565                 570                 575

Leu Ala Asn Met Ile Ser Glu Pro Arg Ile Ser Tyr Gly Asn Asp Ala
                580                 585                 590

Leu Met Pro Ser Leu Thr Glu Thr Lys Thr Thr Val Glu Leu Leu Pro
            595                 600                 605

Val Asn Gly Glu Phe Ser Leu Asp Asp Leu Gln Pro Trp His Ser Phe
            610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
            675                 680                 685

Val Phe Phe Ala Glu Asp Val Gly Ser Asn Lys Gly Ala Ile Ile Gly
            690                 695                 700

Leu Met Val Gly Gly Val Val Ile Ala Thr Val Ile Val Ile Thr Leu
705                 710                 715                 720

Val Lys Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770
```